(12) United States Patent
Zakharov et al.

(10) Patent No.: US 11,540,747 B2
(45) Date of Patent: Jan. 3, 2023

(54) APPARATUS AND A METHOD FOR PASSIVE SCANNING OF AN OBJECT OR A SCENE

(71) Applicant: VIVIOR AG, Zurich (CH)

(72) Inventors: Pavel Zakharov, Volketswil (CH); Michael Mrochen, Zug (CH)

(73) Assignee: VIVIOR AG, Zurich (CH)

( * ) Notice: Subject to any disclaimer, the term of this patent is extended or adjusted under 35 U.S.C. 154(b) by 221 days.

(21) Appl. No.: 16/954,597

(22) PCT Filed: Dec. 7, 2018

(86) PCT No.: PCT/EP2018/083970
§ 371 (c)(1),
(2) Date: Jun. 17, 2020

(87) PCT Pub. No.: WO2019/137709
PCT Pub. Date: Jul. 18, 2019

(65) Prior Publication Data
US 2020/0330003 A1    Oct. 22, 2020

(30) Foreign Application Priority Data
Jan. 9, 2018    (EP) .................................. 18150805

(51) Int. Cl.
| *A61B 5/11* | (2006.01) |
| *A61B 3/00* | (2006.01) |
| *A61B 3/024* | (2006.01) |
| *A61B 3/028* | (2006.01) |
| *G01C 21/20* | (2006.01) |

(Continued)

(52) U.S. Cl.
CPC .......... *A61B 5/1113* (2013.01); *A61B 3/0025* (2013.01); *A61B 3/024* (2013.01); *A61B 3/028* (2013.01); *G01C 21/206* (2013.01); *G01S 7/411* (2013.01); *G01S 7/4802* (2013.01)

(58) Field of Classification Search
CPC ..... A61B 5/1113; A61B 3/0025; A61B 3/024; A61B 3/028; A61B 5/6803; A61B 5/0062; G01C 21/206; G01S 7/411; G01S 7/4802; G01S 17/86; G01S 13/86; G01S 17/88; G01S 17/08; G01S 7/415; G01S 13/08; G01S 15/08; G01S 15/86
See application file for complete search history.

(56) References Cited

U.S. PATENT DOCUMENTS

| 2008/0211768 A1* | 9/2008 | Breen ..................... G06F 3/012 345/157 |
| 2016/0223647 A1* | 8/2016 | Nichols ................... G01S 13/89 |
| 2017/0236299 A1 | 8/2017 | Valkenurg et al. |

FOREIGN PATENT DOCUMENTS

| EP | 3228237 A1 * | 10/2017 | ............. A61B 3/028 |
| EP | 3228237 A1 | 11/2017 | |

\* cited by examiner

*Primary Examiner* — Mohammed A Hasan
(74) *Attorney, Agent, or Firm* — Tarolli, Sundheim, Covell & Tummino LLP

(57) ABSTRACT

The present disclosure relates to an apparatus (100) for passive scanning of an object. The apparatus comprises a distance sensing unit (110) adapted to measure distances to a plurality of points of the object, an orientation sensing unit (120) adapted to determine orientations of the distance sensing unit (110), and a processor (140) adapted to derive information about the object or a scene in which the object is used based on the measured distances and orientations of the distance sensing unit (110).

17 Claims, 18 Drawing Sheets

(51) Int. Cl.
*G01S 7/41* (2006.01)
*G01S 7/48* (2006.01)

(a)

(b)

(c)

(b)

APPARATUS AND A METHOD FOR PASSIVE SCANNING OF AN OBJECT OR A SCENE

CROSS REFERENCES TO RELATED APPLICATIONS

This application filed under 35 U.S.C § 371 is a national phase application of International Application Serial Number PCT/EP2018/083970 filed Dec. 7, 2018, which claims priority to European Patent Application No. 18150805.2, filed Jan. 9, 2018.

TECHNICAL FIELD

The present disclosure generally relates to the field of scanning objects or scenes. More particularly, the present disclosure relates to an apparatus and a method for passive scanning of objects or scenes.

BACKGROUND

Nowadays, active scanning of objects gains increasing attention. Active scanning of objects makes up a significant proportion in future techniques. For example, a self-driving car may actively scan objects such as people and obstacles in a route using an active scanning device provided in the car.

When using such active scanning devices, precise operation is of high importance. Otherwise, such devices lead to malfunction such as causing an accident in case of a self-driving car making use of an active scanning device. Thus, these scanning devices are often technically complex. Moreover, usual active scanning devices do not consider the human's actual interest in the scanned objects.

Active scanning implies control of an active component which facilitates distance measurements (ranging) to a plurality of points of the object or a set of objects for a scene. It typically requires a plurality of sensors arranged in space (like a camera) or movement and/or rotation of a detector in space in a controlled manner or induced variability in exposed points of the object (e.g. obtained with moving probing beam, in RADAR, LIDAR or optical coherence tomography techniques).

Alternatively, scanning can be performed by benefiting from motion of the probing beam or sensor which is not directly related to the scanning activity and not under direct control of the scanning apparatus. For example, the detector can be placed on the moving body part of the user and perform sampling from various angles and positions due to the natural motion of user and/or body parts. This is the idea of/can be regarded as passive scanning.

It is thus an object of the present disclosure to provide an efficient scanning device.

SUMMARY

According to an aspect of the present disclosure, an apparatus (i.e. a passive scanning device) for passive scanning of at least one object is provided. The apparatus may also be referred to as passive scanning device and vice versa. The apparatus comprises (i) a distance sensing unit, (ii) an orientation sensing unit and/or a position sensing unit and (iii) a processor. The distance sensing unit is adapted to measure distances to a plurality of points of or on the at least one object. The orientation sensing unit is adapted to determine orientations of the distance sensing unit. The position sensing unit is adapted to determine positions of the distance sensing unit. The processor is adapted to derive information about the at least one object based on the measured distances to the plurality of points and the determined orientations and/or positions of the distance sensing unit.

Herein, the object may comprise or consist of at least one geometrical primitive such as a surface of the object. The at least one object may be part of a scene, wherein the scene may comprise or consist of one or more objects. The scene may be understood as context in which one or more objects are placed and used.

By way of the above passing scanning, the complexity of the apparatus can be reduced while desired information about the object or scene can still be determined.

The information about the at least one object (in the following, in short, sometimes referred to as "the object"), e.g. the scene, may comprise at least one of a position, a shape, an inclination and a size of the object. Or the information may include or be a topography around or about the object. For example, the information about the object may comprise a movement of the object.

The orientations of the distance sensing unit may be determined, by the orientation sensing unit, when/while the distance sensing unit measures the distances. For example, the movement of the distance sensing unit may be determined, by the orientation sensing unit, when/while the distance sensing unit measures the distances.

The orientation sensing unit may be replaced by, accompanied with or included in a position sensing unit or the other way around. The position sensing unit may be adapted to measure positions of the distance sensing unit or the passive scanning device. The positions of the distance sensing unit may be determined, by the position sensing unit, when/while the distance sensing unit measures the distances. For example, the movement or position of the distance sensing unit may be determined, by the position sensing unit, when/while the distance sensing unit measures the distances.

Herein, passive scanning may be understood as scanning the object in relation to movements of the distance sensing unit and/or as determining the orientations or positions of the distance sensing unit when/while the distance sensing unit measures the distances. For example, passive scanning may be understood as determining the movement of the distance sensing unit when/while the distance sensing unit measures the distances. The movements of the distance sensing unit or passive scanning device may be caused by factors which are not under control of a system or the passive scanning device itself. For example, the movements of the distance sensing unit or passive scanning device may be caused as a consequence of movements of a user on whom the passive scanning device is equipped.

The passive scanning relies on the movement of the sensor not necessarily related to the task of scanning. In this case it is necessary to obtain information about the device position and/or orientation in order to relate measurements to a coordinate space of the scanned object or scene. This can be done with direction sensors, such as an accelerometer, a gyroscope, a magnetometer or position sensors.

The distance sensing unit may be configured to measure one or more distances between the passive scanning device and the object. For example, the distance sensing unit may be provided on the apparatus such that the distance can correspond or be related to a viewing distance which is a distance between eyes of the user and the object. For this purpose, the distance sensing unit may be calibrated in a suitable manner. The distance sensing unit may be configured to measure one or more distances from the distance sensing unit to one or more points of or on the at least one object. The distance sensing unit may be configured to measure a distance in a certain direction. Movements of the distance sensing unit may include rotations of the distance sensing unit. In this way, the distance sensing unit may be configured to measure distances from the distance sensing unit to other points of the object or scene. If the distance sensing unit is mounted on a head of a user, the movements may be caused by head motions/movements of the user. Measuring the distance may be performed multiple times to measure distances between the passive scanning device, for example the eyes of the user, and multiple points of or on the at least one object, e.g. the scene.

The distance sensing unit may use laser-based technology, ultrasound-based technology or any other ranging technology. The distance sensing unit can even be a 3D camera. Range measurements performed by the distance sensing unit can be related to orientations/positions measurements performed by the orientation sensing unit that may include the motion sensor or position sensor.

The orientation sensing unit may be configured to measure angles of the distance sensing unit relative to an origin point. The angles may be named as orientations and be defined to include a vertical angle (vertical orientation) and/or a horizontal angle (horizontal orientation). The origin point may be defined in different ways. As one example, a position of the passive scanning device when it is powered on may be the origin point. Alternatively, the user may set the origin point manually, e.g. by pressing a button or providing a control command to the passive scanning device. It is possible that the origin point may be defined from the statistics of measurements, like a median or centre of weight of measured points. The origin point may be defined in relation to an absolute coordinate system, like the earth magnetic field. The origin point may be construed as an origin of a 3-dimensional coordinate system. In these examples, a forward direction of the passive scanning device at the origin point may be utilized as a base line for measuring the horizontal and/or vertical orientations. The orientation sensing unit may be implemented as or comprise at least one of an accelerometer, a gyroscope sensor, a magnetometer, an altimeter and a compass.

The position sensing unit may be configured to measure positions of the distance sensing unit or the passive scanning device. The positions can be derived from direct measurements, like at least a single coordinate from geolocation, indoor location or altitude (for example, measured by an altimeter). The position sensing unit may be adapted to measure positions of the distance sensing unit relative to an origin point. The origin point may be defined in the same manner as described above. The position can be derived indirectly by sensing motions of the distance sensing unit or the passive scanning device and performing position estimation based on motions (e.g. dead reckoning/path integration). The position sensing unit may be or include one of a geopositioning sensor, an indoor (local) positioning system, a hybrid positioning system or an indirect position estimation unit which may be implemented with inertial (motion) sensors for the dead reckoning or the path integration. The geopositioning sensor may be a location-based sensor, such as GPS, GLONASS or GNSS sensors.

The apparatus may further comprise a memory unit. The memory unit may comprise any suitable calibration data needed for the passive scanning process. For example, the memory may comprise reference data such as reference distances and reference orientations (and/or positions).

The memory unit may be a database having records for various cases of objects (i.e. example objects), scenes (i.e. example scenes) and/or user activities. For example, typical data for different objects may be stored in the memory unit as reference data. The reference data may correspond to coordinates of points or topography of an object in a situation where the object is typically used. The coordinates of points of the object may be defined as a point cloud which is a set of data points in some coordinate system. In a three-dimensional coordinate system, these points are usually defined by X, Y, and Z coordinates, and often are intended to represent the external surface of the object. For example, the reference data for typical use of a desktop Personal Computer (PC) may include coordinate points for a monitor, wherein the coordinate points for the monitor may be located mainly in a range between 0.5 m and 1.5 m in front of the passive scanning device and form a shape similar to the monitor. Further, coordinate points for a keyboard may be included in the reference data as being located closer to the passive scanning device than the coordinate points of the monitor and downward to the coordinate points of the monitor. In this manner, reference data for typical uses of a smartphone, a laptop, a book, a TV and a projection screen may be stored in the memory unit, just to name a few examples without limitation. The reference data can be stored as reference distances (e.g. $\rho$) and reference orientations (e.g. $\phi, \theta$) of the example objects. Conversions between points in Spherical Coordinates and points in 3-dimensional Cartesian Coordinates can be carried out in ways known in the art. Thus, reference data may be stored as either of Spherical coordinate points or 3-dimensional Cartesian coordinate points. The reference data can have a form of any other method of 3-dimensional, such as mesh models, surface-edge-vertex models, generalized-cylinder models, octrees, superquadrics, etc, however, is not limited to these examples. The memory unit may be configured to store the measured distances and orientations and/or positions. The memory unit, e.g. for storing the reference data, can be implemented in the passive scanning device or as a separate entity, e.g. in a different device than the passive scanning device.

The processor may be configured to manage operations of the passive scanning device. The processor may derive information about the at least one object, e.g. the scene. The information may include a position, a shape, a pose, an inclination and/or a size of the object or other measurements of the at least one object. For deriving the information, the processor may be configured to classify an object for which the distances and orientations (and/or positions) are measured as one of the example objects or scenes. The classification may be performed by comparing points of the reference data and the measured data (the measured distances, orientations and/or positions). For example, the processor may be configured to classify the object by finding the most relevant reference data to the measured data. More particularly, the processor may be configured to convert the measured distances and orientations (and/or positions) into coordinate points and compare the converted coordinate points with reference coordinate points (reference data) of each of the example objects, e.g. scenes. Then, the processor may determine the measured object as one of the example objects if the one example object has the largest number of matchings between the converted coordinate points and the reference coordinate points. In this way, the processor may determine which of the example objects has the highest degree of similarity to the measured object. The processor conducting the classification may be implemented in the passive scanning device or in a different device (such as a cloud server for online processing) than the passive scanning device.

The distance sensing unit may include a plurality of distance sensors or a sensor (such as a camera) capable of measuring a plurality of distances from the same orientation and position of a unit, e.g. the main unit (e.g. the sensor). A distance sensor may measure distances in a forward direction of the passive scanning device while other distance sensors may measure distances in other directions, i.e. directions different from the forward direction. For example, one or more distance sensors may be implemented to measure directions inclined to downward, sideward and/or upward directions. The disclosed passive scanning device is thus able to measure multiple distances for multiple objects or multiple points of an object even in case the object comprises or consists of separate parts.

The passive scanning device may be equipped either directly or indirectly to or on a body part of the user. For example, the passive scanning device may be mountable on a head of the user or on spectacles, glasses or the like.

The position sensing unit may be included in the passive scanning device to measure a location and/or a position of the passive scanning device. The position sensing unit may be part of the orientation sensing unit or be implemented therein or may be separate unit. The position sensing unit may be adapted to measure at least one coordinate of the passive scanning device in space. The position sensing unit may include at least one of geolocation systems (such as global positioning system (GPS), GLONASS or GNSS sensors), an altimeter system, an indoor positioning system and a hybrid positioning system. Elevation as well can be measured from a geopositioning sensor or with an altimeter. The position sensing unit may be adapted to measure movements of the passive scanning device and thus of the user when the passive scanning device is equipped on the body part of the user. The measured position may serve as an input with the measured data from the distance sensing unit for the classification of the at least one object, e.g. scene. The application of the measured position for the classification may be defined in the same way as the use of the measured data from the orientation sensing unit.

The indoor positioning system (IPS) may be understood as a system to locate objects or people inside a building using radio waves, magnetic fields, acoustic signals, or other sensory information collected by mobile devices. There are several commercial systems on the market, but there is no standard for an IPS system. IPSs use different technologies, including distance measurement to nearby anchor nodes (nodes with known positions, e.g., WiFi access points), magnetic positioning, dead reckoning and the like. They either actively locate mobile devices and tags or provide ambient location or environmental context for devices to get sensed. The system might include information from other systems to cope for physical ambiguity and to enable error compensation. Detecting the device's orientation (often referred to as the compass direction in order to disambiguate it from smartphone vertical orientation) can be achieved either by detecting landmarks inside images taken in real time, or by using trilateration with beacons.

The processor may classify an activity of the user based on the measured movements or the derived information about the at least one object. For example, if an average speed determined from the measured movements is between 3 km/h and 5 km/h, the processor may determine that the user is walking. For an average speed from 5 km/h to 20 km/h, it can be concluded that running is the activity of the user. For an average speed over 20 km/h, the processor may specify that the user is riding a bike or a car or the like. The above may be named activity recognition.

The relative position of the passive scanning device can be derived from the movement measured with inertial sensors, which is known as dead reckoning. For example, being able to detect acceleration of device with an accelerometer allows estimating an expected position of the device in space in relation to the point of origin. The relative position in combination with distance measurements can be used to build the coordinate point cloud.

The processor may be configured to derive at least one of a position, a shape, an inclination, a pose and a size of the object from the measured distances and orientations (and/or positions). The processor may be configured to determine an activity of the user or an environment where the user is located based on/from the derived at least one of the position, shape, inclination and size of the object. The position, shape, inclination, pose and/or size of the object may be derivable from the coordinate points of the measured distances and orientations (and/or positions). When the coordinate points are plotted in 3-dimensional coordinates, assemblage of the coordinate points may form a contour of the object, from which the position, shape, inclination, pose and/or size may be derivable. The measured positions or movements of the passive scanning device may be supplemented to determine the user's activity. For example, a trace of positions of the object may provide a hint for determining whether the user is in indoor or outdoor. The length of a straight-line of the trace may be longer than that of a usual indoor activity. From this, it may be derived that the user is outdoor or indoor. As another example, characteristic movements of the sensor, related to movements of the user or the body part can serve as an input for activity recognition, such as specific acceleration/rotation patterns during walking, running or even reading can help to better classify activities. Therefore, the disclosed passive scanning device is able to efficiently classify the user's activity.

A motion sensor, e.g. an inertial sensor, may be included in the passive scanning device. The motion sensor may be configured to measure an amount of motion of the apparatus/passive scanning device. For example, the motion sensor may be configured to measure an acceleration of movements of the passive scanning device. For example, the motion sensor may be part of or implemented in the orientation sensing unit or may be a separate entity. When the passive scanning device measures the distances and orientations (and/or positions), the processor may discard distances and orientations (and/or positions) measured in a predetermined time period when/in which the motion sensor has measured that an amount of motion and/or the acceleration is higher than a threshold value. For example, considering a user of a desktop PC, his/her head may suddenly move with comparatively high acceleration when he/she hears the sound of a ringing telephone. Even though the user's attention is drawn to the telephone, since it is not the object of interest of the user, he/she may quickly turn his/her head back to the desktop PC. Thus, the processor may discard distances and orientations (and/or positions) measured with respect to the telephone since the acceleration of the movement to turn the head into the direction of the telephone is higher than a usual acceleration of utilizing the desktop PC. The threshold value and the predetermined time period may be freely selected by a user, a device setting or an expert like a surgeon who needs the result of the passive scanning. The threshold value may be defined as 'N' multiples (e.g. N times, wherein N is greater than 1, preferably 2 or 3) of an average acceleration value of the passive scanning device for a period of the measurements of the distances and orientations (and/or positions). The predetermined time period may be defined as 'M' multiples (e.g. M times, wherein M is less than 1 and greater than 0, preferably 0.01 to 0.05) of a total time period of the measurements of the distances and orientations (and/or positions) in the passive scanning device. The disclosed passive scanning device is thus able to save device resources for processing meaningless data and enhance precision of a result of the passive scanning of the object.

The activity information, extracted directly from motion sensors, like typical patterns of head/body motion, walking, reading, etc, may serve as an independent input to classification of the at least one object, e.g. scene. Additionally, activity information can be provided directly by user via user interface of the device or from the other sensors or devices, such as smartphones or smartwatches worn by the user and connected to scanning device by means of e.g. body area network.

The processor may be configured to classify the object or scene as one of example objects or scenes when differences between the measured distances and orientations (or positions) and the stored reference distances and reference orientations (and/or positions) are less/smaller than predetermined amounts. Since circumstances for using the same object for different users may vary, there is a possibility that data for some kinds of objects and some variations depending on characteristics and circumstances of the users cannot be stored as the reference data. Thus, even if there are differences between the measured data (distances and orientations (and/or positions)) and the reference data, offset values may be allowed to the differences in the range of certain amounts. Upper limits for the offset values (predetermined amounts) may be freely selected by a user, a device setting or an expert. The upper limits may be set differently based on usual distances for the objects. For example, upper limits of an object, such as a laptop, a PC, a book or a smartphone that may be used at comparatively near positions from a user may be set less than those of an object, such as a TV or a projection screen that may be usually located further apart from the user. For example, an offset for a desktop PC may be up to 60 cm whereas an offset for a 60 inches TV may be up to 3 m.

Additionally, limits of the object or activities may be derived from measurement statistics collected during known activities, for example, when a user has manually indicated (tagged) the type of activity via the user interface during, before or after performing such activity. For example, a user might be able to tag activities while reviewing measurements by means of a smartphone app or through a web-interface. With this information an algorithm can be trained in a supervised or unsupervised manner to recognize similar activities automatically from the measurements. Such recognition can be performed on the real time data already during measurements or on the recorded data collected in the past. An algorithm may combine data from multiple users in order to more accurately recognize and classify activities.

The processor may be configured to classify the object or scene using morphological information derived from the measured data. The morphological information may be or include shape of the object, composition of the object and/or locations of the objects on the scene.

The processor may be configured to convert the measured distances and orientations (and/or positions) to coordinate points, compare the converted coordinate points with the stored reference distances and orientations (and/or positions), and classify the object as one object of the example objects when reference distances and orientations (and/or positions) of the one object have the largest number of matching points (as compared to the other example objects) with the converted coordinate points. The reference distances and orientations (and/or positions) for each of the example objects may be stored in formats of Spherical coordinate points and/or Cartesian coordinate points. The processor may be configured to convert the measured distances and orientations (and/or positions) to Spherical coordinate points and/or Cartesian coordinate points and then to check how many points of the measured data match the reference Spherical coordinate points and/or Cartesian coordinate points of each of the example objects. The processor may determine one object among the example objects when the reference Spherical coordinate points and/or Cartesian coordinate points of the one object have the largest number of points matching the converted coordinate points.

The processor may be configured to convert the measured distances and orientations (and/or positions) and/or the at least one coordinate to a (geometrical) spatial model of the object or scene, compare the spatial model with stored reference spatial models, classify the object or scene as one of example objects or scenes when a reference spatial model for the one example object or scene have the largest matching score with the spatial model (as compared to the other reference spatial models).

The memory unit may be configured to store the reference spatial models.

According to another aspect of the present disclosure, a method for passive scanning of at least one object is provided. The method comprises the steps of measuring distances to a plurality of points of or on the at least one object, determining orientations and/or position of the passive scanning device, and deriving information about the at least one object based on the measured distances and the determined orientations and/or positions. The method may be carried out by a passive scanning device. The passive scanning device may be or comprise the apparatus according to the first aspect described herein.

The orientations and/or positions may be determined while the distances are measured.

The information about the object or scene may comprise at least one of a position, a shape, an inclination and a size of the object. For example, the information about the object may comprise a movement of the object.

The method may further include storing reference distances and reference orientations (and/or positions) on a plurality of example objects or reference spatial models. The method may further include deriving the information about the object by comparing the measured data with the stored reference data.

The distances may be measured by a plurality of distance sensors.

The distances and the orientations (and/or positions) may be measured and determined by the passive scanning device equipped on or to a body part of the user.

The method may further comprise measuring a position or a movement of the passive scanning device by using at least one of a global, an indoor and hybrid positioning system or the like.

The method may further comprise classifying or determining an activity of the user or an environment around the user from the derived information about the object.

The method may further comprise measuring an amount of motion or an acceleration of movements of the passive scanning device, and discarding distances and orientations (and/or positions) measured in a predetermined time period when the measured amount of motion or acceleration is higher than a threshold value.

In the method, the step of classifying may include determining differences between the measured distances and orientations (and/or positions) and the stored reference distances and reference orientations (and/or positions), respectively, and classifying the object as the one of the example objects when the differences are less than predetermined amounts.

The method may further comprise converting the measured distances and the determined orientations (and/or positions) to coordinate points. The method may further comprise comparing the converted coordinate points with stored reference distances and reference orientations (and/or positions). The method may further comprise classifying the object as one object of example objects when the reference distances and reference orientations (and/or positions) for the one object have the largest number of matching points with the converted coordinate points.

The method may further comprise converting the measured distances and the determined orientations (and/or positions) and/or the at least one coordinate to a (geometrical) spatial model of the object or scene, comparing the spatial model with stored reference spatial models, classifying the object or scene as one of example objects or scenes when the reference spatial model for the one example object or scene has the largest matching score with the spatial model.

The method may further comprises estimating an activity-related viewing distance of the user by applying a statistical method to the derived information about the at least one object.

The method may further comprise identifying visual requirements of the user by applying a statistical method to the derived information about the object or scene.

The identifying visual requirements may comprise identifying a user activity based on the derived information about the at least one object, and identifying the visual requirements based on the user activity.

The identifying visual requirements may comprise identifying a user activity based on the derived information about the at least one object, identifying a viewing distance of a user based on the user activity, and identifying the visual requirements based on the viewing distance of the user.

The method may further comprise determining a refractive solution for the user based on the visual requirements, wherein the refractive solution is one of an ablation profile for refractive surgery, an ophthalmic implant and an ophthalmic lens, wherein the ophthalmic lens is one of an intraocular lens, a contact lens and a spectacles lens.

Specific examples or explanations for the method may be complemented by the explanations described above for the passive scanning device in the present disclosure.

BRIEF DESCRIPTION OF THE DRAWINGS

In the following, the present disclosure will further be described with reference to exemplary implementations illustrated in the figures, in which.

DETAILED DESCRIPTION

In the following description, for purposes of explanation and not limitation, specific details are set forth in order to provide a thorough understanding of the present disclosure. It will be apparent to one skilled in the art that the present disclosure may be practiced in other implementations that depart from these specific details.

Those skilled in the art will further appreciate that functions explained herein below may be implemented using individual hardware circuitry, using software functioning in conjunction with one or more processors, e.g. a programmed microprocessor or a general purpose computer, using an Application Specific Integrated Circuit (ASIC) and/or using one or more Digital Signal Processors (DSPs). It will also be appreciated that when the present disclosure is described as a method, it may also be embodied in a computer processor arrangement and a memory arrangement coupled to a processor arrangement, wherein the memory arrangement is encoded with or stores one or more programs or corresponding code to cause the processor arrangement to perform or control the methods disclosed herein when executed by the processor arrangement.

Figure 1:
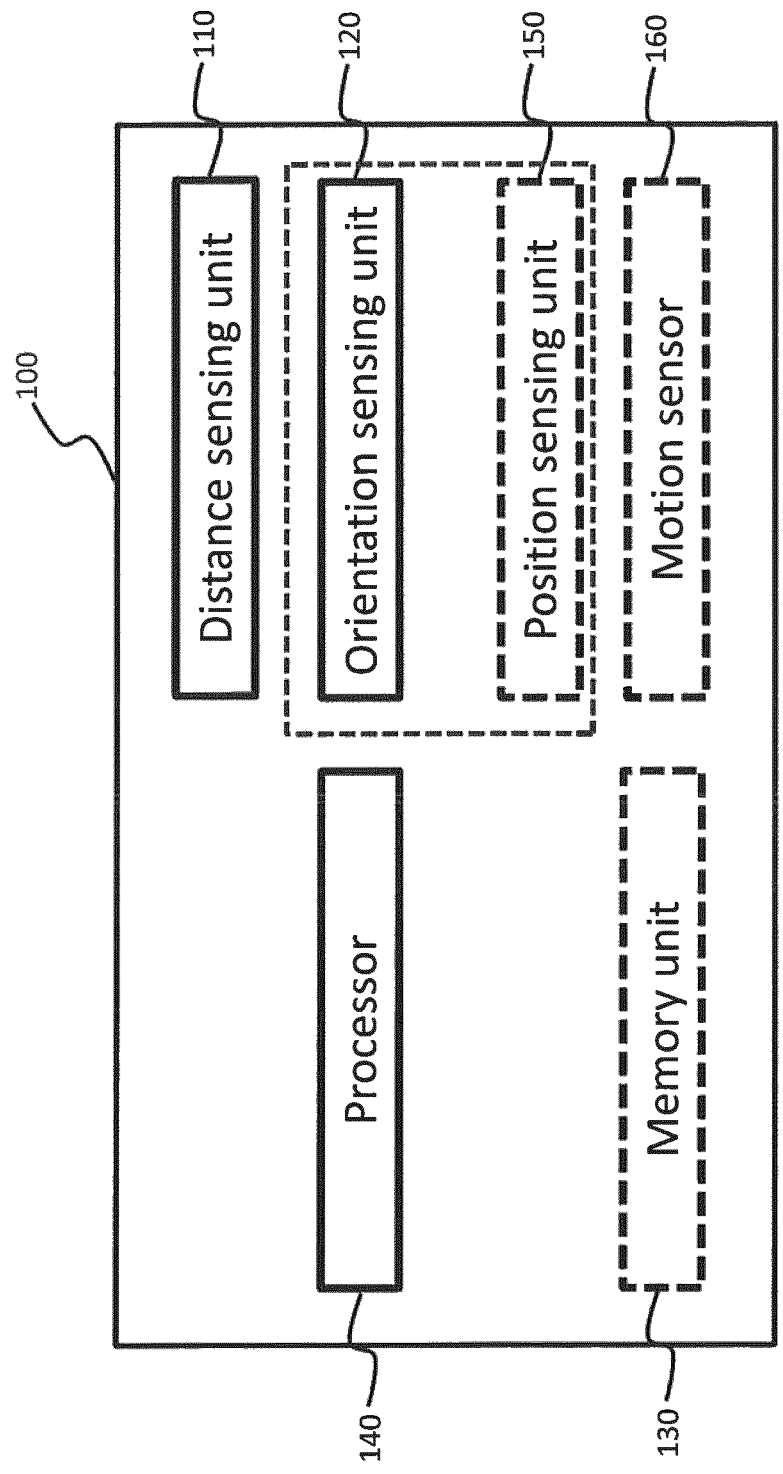
FIG. 1 illustrates an example of a passive scanning device according to the present disclosure.

FIG. 1 illustrates an example of a passive scanning device according to the present disclosure. In the present example, the passive scanning device 100 comprises a distance sensing unit 110, an orientation sensing unit 120, and/or a processor 140. The passive scanning device 100 may optionally further comprise a memory unit 130, a position sensing unit 150 and/or a motion sensor 160. Instead of or in addition to the orientation sensing unit 120, the position sensing unit 150 may be a mandatory component, while the orientation sensing unit 120 may be an optional component in the former case. The passive scanning device 100 may be equipped on a body part of the user. The passive scanning device 100 can be mounted on a head of the user or on spectacles/glasses or the like. The orientation sensing unit 120 may be replaced by, accompanied with or included in the position sensing unit 150. The motion sensor 160 may be included in the distance sensing unit 110 as a movement sensor 20 as will be explained in the following.

The distance sensing unit 110 may be configured to measure distances to a plurality of points of an object. The distance sensing unit 110 may be configured to measure a distance between the passive scanning device 100 and the object. For example, the distance sensing unit 110 may be equipped in the passive scanning device 100 such that the distance can correspond or be related to a viewing distance which is a distance between eyes of the user and the object. The distance sensing unit 110 may be configured to measure one or more distances from the distance sensing unit 110 to one or more points of or on the object or scene. The distance sensing unit 110 may be configured to measure a distance in a certain direction. In the present example, movements include rotations and/or displacements of the distance sensing unit. Thus, the distance sensing unit 110 may be configured to measure distances from the distance sensing unit 110 to other points of the object or scene. If the distance sensing unit 110 is mounted on a head of a user, the movements may be caused by natural head motions of the user. Measuring the distance may be performed multiple times to measure distances between the passive scanning device 100, for example the eyes of the user, and multiple points of the object or scene.

The distance sensing unit 110 may include a plurality of distance sensors or a sensor (such as a camera) capable of measuring a plurality of distances. A distance sensor may measure distances in a forward direction of the passive scanning device 100 while other distance sensors may measure distances in other directions than the forward direction. For example, one or more distance sensors may be implemented to measure distances in downward, sideward and/or upward directions. The disclosed passive scanning device 100 is thus able to measure multiple distances for multiple objects or multiple points of an object even when the object consists of separate parts.

The orientation sensing unit 120 may be configured to determine orientations of the distance sensing unit 110. The orientation sensing unit 120 may be configured to measure angles of the distance sensing unit 110 relative to an origin point. The angles may be defined to include a vertical angle (vertical orientation) and/or a horizontal angle (horizontal orientation). The origin point may be defined in different ways. As one example, a position of the passive scanning device 100 when it is powered on may be the origin point. Or it may be possible that the user sets the origin point manually, e.g. by pressing a button or providing a control command to the passive scanning device 100. The origin point may be derived statistically from a set of points. The origin point may be defined in relation to an absolute coordinate system, like Earth magnetic field. The origin point may be construed as an origin of 3-dimensional coordinates system. In these examples, a forward direction of the passive scanning device 100 at the origin point may be utilized as a base line for measuring the horizontal and/or vertical orientations. The orientation sensing unit 120 may be implemented as or comprise at least one of an accelerometer, a gyroscope sensor, a magnetometer, an altimeter and a compass.

The memory unit 130 may comprise any suitable calibration data needed for the passive scanning process. For example, the memory unit 130 may comprise reference data such as reference distances and reference orientations (and/or reference positions). The memory unit 130 may be a database having records for various cases of objects (i.e. example objects), scenes (i.e. example scenes) and/or user activities. For example, typical data for different objects or scenes may be stored in the memory unit 130 as reference data. The reference data may correspond to coordinates of points or topography of an object in a situation where the object is typically used. The coordinates of points of the object may be defined as a point cloud which is a set of data points in some coordinate system. In a three-dimensional coordinate system, these points are usually defined by X, Y, and Z coordinates, and often are intended to represent the external surface of the object. For example, the reference data for typical use of a desktop Personal Computer (PC) may include coordinate points for a monitor, wherein the coordinate points for the monitor may be located mainly in range between 0.5 m and 1.5 m in front of the passive scanning device and form a shape similar to that of the monitor. Further, coordinate points for a keyboard may be included in the reference data as being located closer to the passive scanning device 100 than the coordinate points of the monitor and downward to the coordinate points of the monitor. In a similar manner, reference data for typical uses of a smartphone, a laptop, a book, a TV and a projection screen may be stored in the memory unit 130. The reference data can be stored as reference distances (e.g. $\rho$) and reference orientations (e.g. $\phi$, $\theta$) of the example objects, which may correspond to Spherical coordinate points. The Spherical coordinate points can be converted to points in 3-dimensional Cartesian coordinates with known mathematical methods. The memory unit 130 may store the measured distances and orientations (and/or positions). The memory unit 130 can be implemented in a different device than the passive scanning device 100 or in/as part of the passive scanning device 100. The reference data can have a form of any other method of 3-dimensional, such as mesh models, surface-edge-vertex models, generalized-cylinder models, octrees, superquadrics, etc, however, is not limited to the exampled forms. The memory unit 130 may be configured to store the reference spatial models.

The processor 140 may manage operations of the passive scanning device 100. The processor 140 may derive information about the object or scene. The information may include a position, a shape, an inclination, a size, a pose and/or a kind of the object or scene. Or the information may include or be topography around or about the object. For deriving the information, the processor 140 may classify an object for which the distances and orientations (and/or positions) are measured as one of the example objects or scenes. The classification may be performed by comparing points of the reference data and the measured data (i.e. measured distances and orientations (and/or positions)). For example, the processor 140 may classify the object by finding the most relevant reference data to the measured distances and orientations (and/or positions). More particularly, the processor 140 may convert the measured distances and orientations (and/or positions) to coordinate points and compare the converted coordinate points with reference coordinate points (reference data) of each of the example objects or scenes, then the processor 140 may determine the measure object or scene as one of the example objects or scenes if the one has the largest number of matchings between the converted coordinate points and the reference coordinate points. The processor 140 may convert coordinate points to geometrical models of the objects and determine object or scene by matching measured objects with templates from calibration data. The processor 140 conducting the classification may be implemented in a different device (such as a cloud sever for online processing) than the passive scanning device 100 or in/as part of the passive scanning device 100.

The processor 140 may derive at least one of a position, a shape, an inclination, a pose and a size of the object or scene from the measured distances and orientations (and/or positions). The processor 140 may determine an activity of the user or an environment where the user is located based on the derived at least one of the position, shape, inclination, pose and size of the object or scene. The position, shape, inclination and/or size of the object may be derivable from the coordinate points of the measured distances and orientations (and/or positions). When the coordinate points are plotted in 3-dimensional coordinate, assemblage of the coordinate points may form contour of the object, from which the position, shape, inclination, pose and/or size may be derivable.

The processor 140 may classify the object or scene as the one of the example objects or scenes when differences between the measured distances and orientations (and/or positions) and the stored reference distances and reference orientations (and/or positions) are less than predetermined amounts. Since circumstances for using the same object for different users may vary, there is a possibility that data for some kinds of objects and some variations depending on characteristics and circumstances of the users cannot be stored as the reference data. Thus, even if there are differences between the measured data (distances and orientations (and/or positions)) and the reference data, offset values may be allowed to the differences in range of certain amount. Upper limits for the offset values (predetermined amounts) may be freely selected by a user, a device setting, a doctor or a surgeon. The upper limits may be set differently based on usual distances for the objects. For example, upper limits of an object, such as a laptop, a PC, a book or a smartphone that may be used at comparatively near positions from a user may be set less than those of an object, such as a TV or a projection screen that may be usually located apart from the user. For example, offset for a desktop PC may be allowed up to 60 centimeters whereas offset for a 60 inches TV may be allowed up to 3 meters.

The processor 140 may be configured to classify the object or scene using morphological information derived from the measured data. The morphological information may be or include a shape of the object, composition of the object and/or locations of the objects on the scene.

The processor 140 may convert the measured distances and orientations (and/or positions) to coordinate points, compare the converted coordinate points with the stored reference distances and orientations (and/or positions), and classify the object or scene as one object of the example objects or scenes when reference distance and orientations (and/or positions) of the one object have the largest number of matching points with the converted coordinate points. The reference distances and orientations (and/or positions) for each of the example objects or scene may be stored in formats of Spherical coordinate points and/or Cartesian coordinate points. The processor 140 may convert the measured distances and orientations (and/or positions) to Spherical coordinate points and/or Cartesian coordinate points. Then, the processor 140 may check how many points of the measured data match the reference Spherical coordinate points and/or Cartesian coordinate points of the each of the example objects or scene. The processor 140 may determine one object among the example objects or scene when the reference Spherical coordinate points and/or Cartesian coordinate points of the one object or scene have the largest number of points matching to the converted coordinate points. The offsets delineated above may be allowed to the reference data when the passive scanning 100 device checks the number of points matching to the converted coordinate points.

The processor 140 may be configured to convert the measured distances and orientations (and/or positions) and/or the at least one coordinate to spatial model of the object or scene, compare the spatial model with stored reference spatial models, classify the object or scene as one of example objects or scenes when the reference spatial model for the one example object or scene have the largest matching score with the spatial model.

The example scenes or objects can be defined as cloud points in a coordinate system. The cloud points (or point cloud) can be a set of geometrical primitives (e.g. cylinders, cubes with their parameters), locations, poses and/or objects (e.g. laptop, desk surface, etc with their locations, poses, etc).

The passive scanning device 100 may optionally include a position sensing unit 150 to measure a location and/or a position of the passive scanning device 100. The position sensing unit 150 may be part of the orientation sensing unit 120 or be implemented therein or may be separate unit. The position sensing unit 150 may be adapted to measure at least one coordinate of the passive scanning device in space. The position sensing unit 150 may include at least one of geolocation systems such as global positioning system (GPS), GLONASS or GNSS sensors, an indoor positioning system and a hybrid positioning system. Elevation as well, can be measured from the positioning sensor or with an altimeter. The position sensing unit 150 may be adapted to measure movements of the user when the passive scanning device 100 is equipped on the body part of the user. The position sensing unit 150 may be configured to measure positions of the distance sensing unit 110 or the passive scanning device 100. The positions can be derived from direct measurements, like at least a single coordinate from geolocation, indoor location or altitude (from an altimeter). The position sensing unit 150 may be adapted to measure positions of the distance sensing unit 110 relative to an origin point. The origin point may be defined in the same manner of the description above. The position can be derived indirectly by sensing motions of the distance sensing unit 110 or the passive scanning device 100 and performing position estimation based on motions (e.g. dead reckoning/path integration). The position sensing 150 unit may be or include one of a geopositioning sensor, an indoor (local) positioning system, a hybrid positioning system or an indirect position estimation unit which may be implemented with inertial (motion) sensors for the dead reckoning or the path integration. The geopositioning sensor may be a location-based sensor, such as GPS, GLONASS or GNSS sensors. The measure position may serve as an input with the measured data from the distance sensing unit for the classification of the object or scene. The application of the measured position for the classification may be defined as the same way as the use of the measured data from the orientation sensing unit 120.

The position sensing unit 150 may be adapted to measure positions of the distance sensing unit 110 or the passive scanning device 100. The positions of the distance sensing unit 110 may be determined, by the position sensing unit 150, when/while the distance sensing unit 110 measures the distances. For example, the movement or position of the distance sensing unit 110 may be determined, by the position sensing unit 150, when/while the distance sensing unit 110 measures the distances.

The processor 140 may classify the user's activities based on the measured movements or the derived information from the measurements. For example, if an average speed determined from the measured movements is between 3 km/h and 5 km/h, the processor 140 may determine that the user is walking. For an average speed from 5 km/h to 20 km/h, running can be the activity of the user. For an average speed over 20 km/h, the processor 140 may specify that the user is riding a car or the like. The measured locations or positions may be supplemented to determine the user's activity. For example, trace of the locations or positions of the object may provide a hint for determining whether the user is in an indoor or outdoor environment. Length of straight-line of the trace longer than that of usual indoor activity may be regarded as an indication that the user's activity is an outdoor activity. Therefore, the disclosed passive scanning device 100 is able to efficiently and precisely classify the user's activity. Relative position of the passive scanning device 100 can be derived from the movement measured with inertial sensors, which is known as dead reckoning. For example, being able to detect acceleration of device with an accelerometer or the motion sensor 160 allows estimating expected position of the device in space in relation to point of origin. Relative position in combination with distance measurements can be used to build the coordinate point cloud.

The passive scanning device 100 may optionally include a motion sensor 160 to measure acceleration of movements of the passive scanning device 100. For example, the motion sensor 160 may be part of or implemented in the orientation sensing unit 120 or the distance sensing unit 110. When the passive scanning device 100 measures the distances and orientations (and/or positions), the processor 140 may discard distances and orientations (and/or positions) measured in a predetermined time period in which the acceleration or amount of motion measured by the motion sensor 160 is higher than a threshold value. For example, imagine the situation that the head of a user of a desktop PC suddenly moves with comparatively high acceleration when he/she hears a sound of a telephone. Even though the user's attention is drawn to the telephone, since it is not the object of interest of the user, he/she may turn his/her head back to desktop PC shortly thereafter. Thus, the processor 140 can discard distances and orientations (and/or positions) measured on the telephone since the acceleration of the movement to stare into the direction of the telephone is higher than a usual acceleration occurring during utilizing the desktop PC. The threshold value and the predetermined time period may be freely selected by a user, a device setting, a doctor or a surgeon who intends to evaluate the result of the passive scanning. The threshold value may be defined as 'N' multiples (e.g. N times, wherein N is greater than 1, preferably 2 or 3) of an average acceleration value of the passive scanning device 100 for a period of the measurement of the distances and orientations (and/or positions). The predetermined time period may be defined as 'M' multiples (e.g. M times, wherein M is less than 1 and greater than 0, preferably 0.01 to 0.05) of a total time period of the measurement of the distances and orientations (and/or positions) in the passive scanning device 100. The disclosed passive scanning device 100 is thus able to save device resources for processing the meaningless data and enhance precision of a result of passive scanning of the object. The activity information, extracted directly from motion sensors, like typical patterns of head/body motion, walking, reading, etc, may serve as an independent input to classification of the object or scene.

Figure 2:
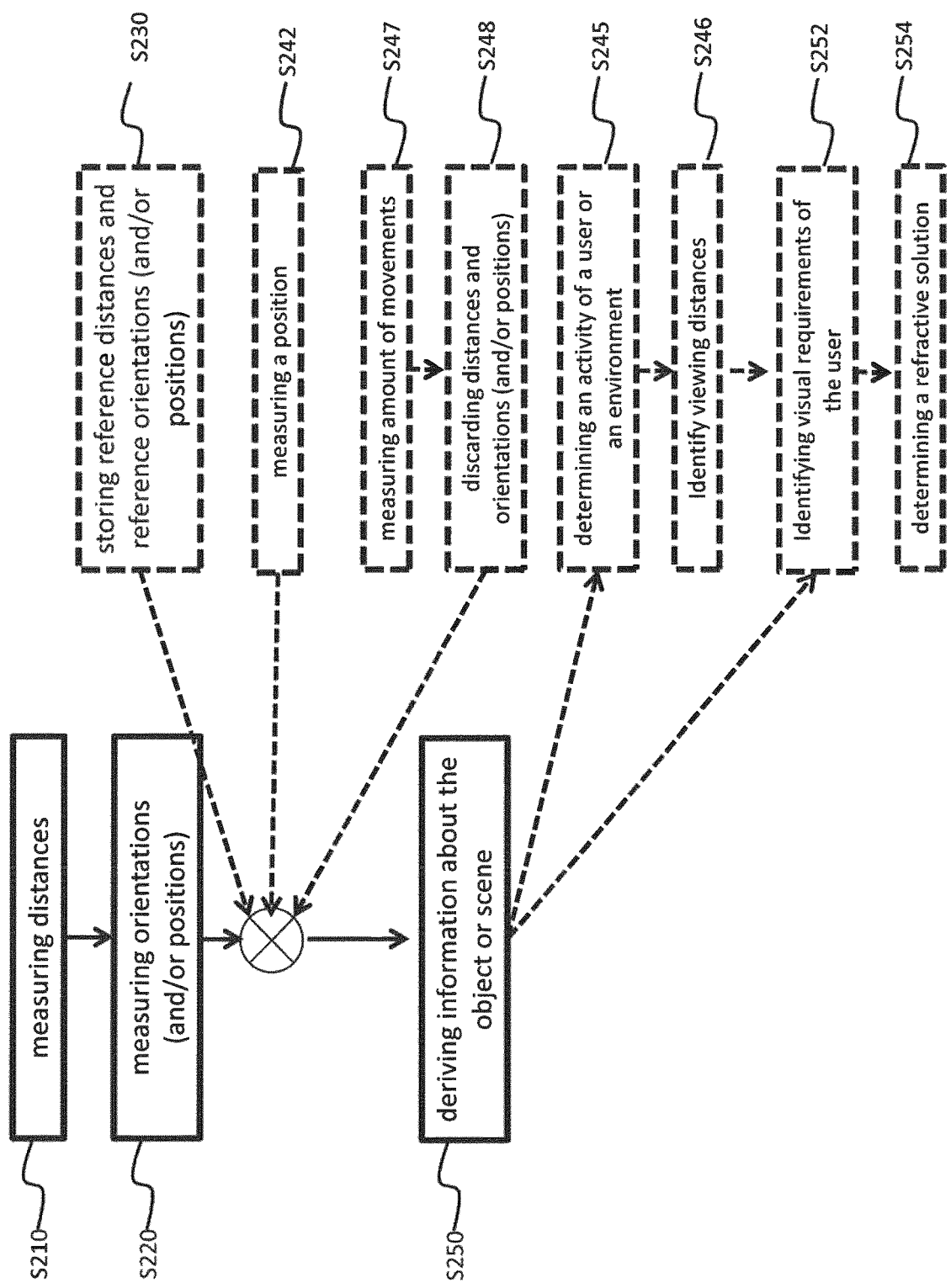
FIG. 2 illustrates a flow diagram corresponding to a method of the present disclosure.

FIG. 2 illustrates a flow diagram corresponding to a method of the present disclosure. In the method, distances to a plurality of points of the object or scene may be measured (S210). Orientations (and/or positions) of the passive scanning device 100 may be determined before, after or at the same time of measuring the distances (S220). Based on the measured data (measured distances and orientations (and/or positions)), information about the object may be derived (S250).

The distances and the orientations (and/or positions) are measured and determined by the passive scanning device 100 equipped on a body part of the user.

The information about the object comprises or is at least one of a position, a shape, an inclination, a pose and a size of the object or scene, for example a movement of the object.

The measured distances and orientations (and/or positions) may be recorded in memory unit 130. The measured data may be recorded as distances (e.g. $\rho$) and orientations (e.g. $\phi$, $\theta$) of Spherical coordinates. Thus, the combinations of the measured distances and orientations (and/or positions) may form plotted points in the space. The reference data including the reference distances and reference orientations (and/or positions) of the example objects or scenes may be stored (S230) in the memory unit 130. It is also possible that the reference data can be stored in advance of the measurements of the distances and orientations (and/or positions) in the memory unit 130.

Optionally, measuring a position of the passive scanning device 100 may be performed (S242). Measuring positions may result in measuring a speed of the passive scanning device 100 in combination with duration of the measurements. The measurement of positions may provide traces of movements of the passive scanning device 100. The measured locations, speeds and/or traces may be used in addition to the measured data to classify an object or specify an environment around the passive scanning device 100. Thus, preciseness of the classification can be improved.

Optionally, the derivation of the information about at least one of the position, shape, inclination, pose and size of the object or scene, for example the movement of the object may be performed based on plotted points of the measured data of the object. The derived information of the object or scene in addition to the measured data may be used to classify an activity of a user or an environment around the passive scanning device 100 or the user (S245).

Optionally, measuring an amount of movements of the passive scanning device 100 may be performed (S247). The measured amount of movements may be used as an indicator for discarding the measured data (S248). As described above, higher acceleration than a threshold value of the passive scanning device 100 may be the indication for the necessity of discarding the measured data during a predetermined duration when the higher acceleration is/has been measured.

Optionally, deriving of information about the object or scene may comprise or be replaced by steps including converting the measured distances and the determined orientations (and/or positions) to coordinate points, comparing the converted coordinate points with stored reference distances and reference orientations (and/or positions), and classifying the object or scene as one object of example objects or scenes when the reference distances and reference orientations (and/or positions) for the one object or scene have the largest number of matching points with the converted coordinate points.

Optionally, deriving of information about the object or scene may comprise or be replaced by steps including converting the measured distances and the determined orientations (and/or positions) and/or the at least one coordinate to spatial model of the object or scene, comparing the spatial model with stored reference spatial models and classifying the object or scene as one of example objects or scenes when the reference spatial model for the one example object or scene have the largest number of matching score with the spatial model.

Optionally, the method may further comprise identifying (S252) visual requirements of the user by applying a statistical method to the derived information about the object or scene. The method my further comprise identifying (S252) visual requirements of the user by applying a statistical method to the determined activity of the user or the environment. In the statistical method, weights lager than or equal to 1 may be applied to the derived information when it is derived from the measurements of which frequency is higher than or equal to the predetermined value, whereas weights equal to 0 or larger than 0 and smaller than 1 may be applied to the derived information when it is derived from the measurements of which frequency is lower than the predetermined value.

Optionally, the method may further comprise determining (S246) the viewing distance based on the coordinates of points and/or geometrical model of the scene and activity performed by the user. For example, if a scene is recognized as a desktop with a personal computer and activity is classified as a computer work, the relevant viewing distance is a distance from the user eyes to the computer display, represented by geometrical model or the set of points in space.

Optionally, the method may further comprise determining (S254) a refractive solution for the user based on the visual requirements, wherein the refractive solution is one of an ablation profile for refractive surgery, an ophthalmic implant and an ophthalmic lens, wherein the ophthalmic lens is one of an intraocular lens, a contact lens and a spectacles lens.

Together with the results of the optionally described steps (S242, S245, S246, S247 and/or S248), the classification (S250) of the objection can be done more precisely.

Figure 3:
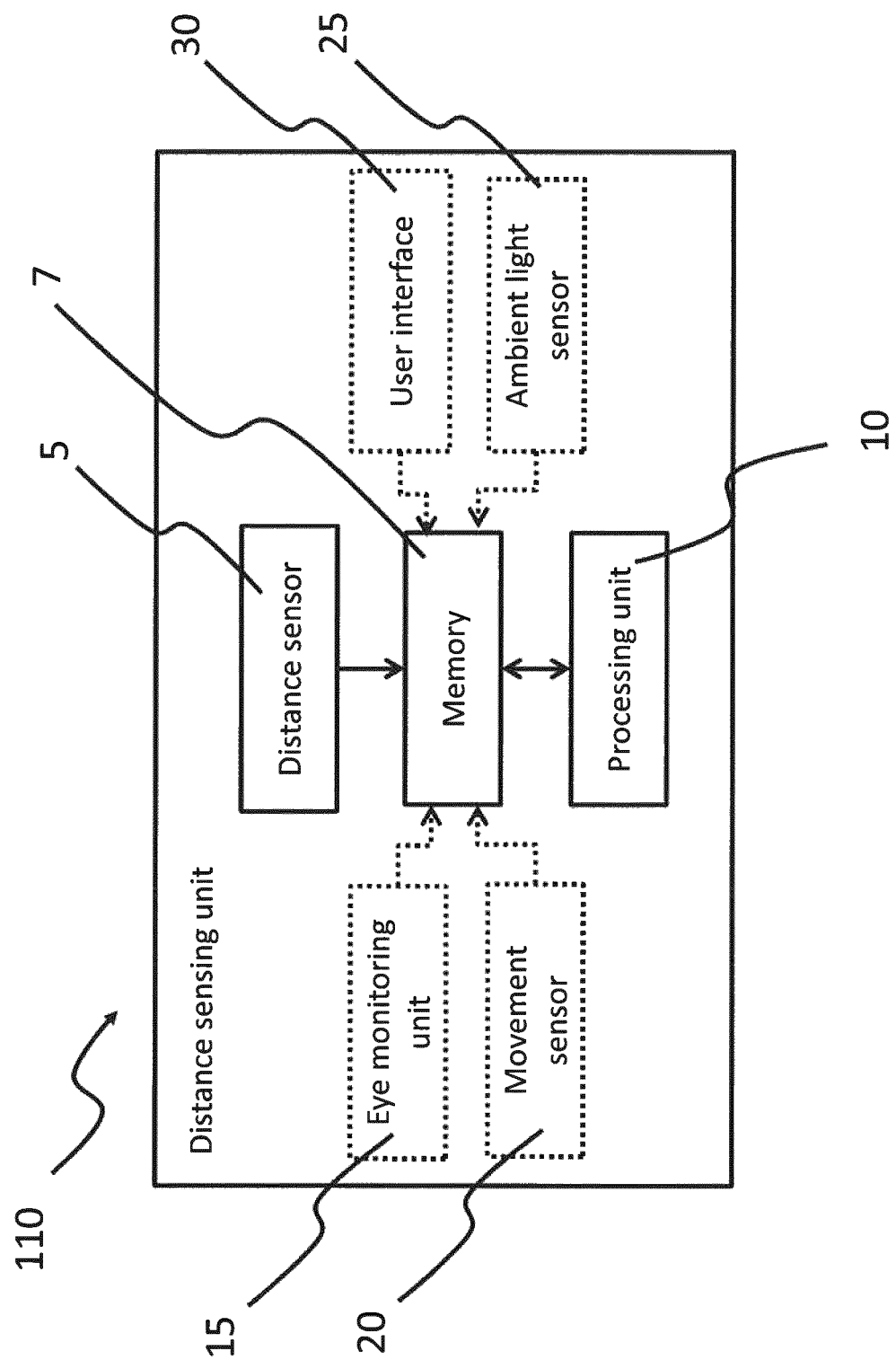
FIG. 3 illustrates an example of a distance sensing unit 110 according to the present disclosure.

FIG. 3 illustrates an example of a distance sensing unit 110 according to the present disclosure. The distance sensing unit 110 may comprise a distance sensor (or a plurality of distance sensors) 5, a memory unit 7 and/or a processing unit 10. Functions of the memory unit 7 and/or processing unit 10 can be performed by the processor 130 and the memory 140 of the passive scanning device 100 described above, and the memory unit 7 and/or processing unit 10 may be omitted in the distance sensing unit 1. Optionally, the distance sensing unit 110 may comprise an eye monitor unit 15, a movement sensor 20, an ambient light sensor and/or a user interface 30. The different units 5, 7, 10, 15, 20, 25 of the distance sensing unit 110 can be realised in one and the same device 110 or can be distributed in two or more separate devices to form the distance sensing unit 110. Further details of the distance sensing unit 110 will now be described with respect to FIG. 4.

Figure 4:
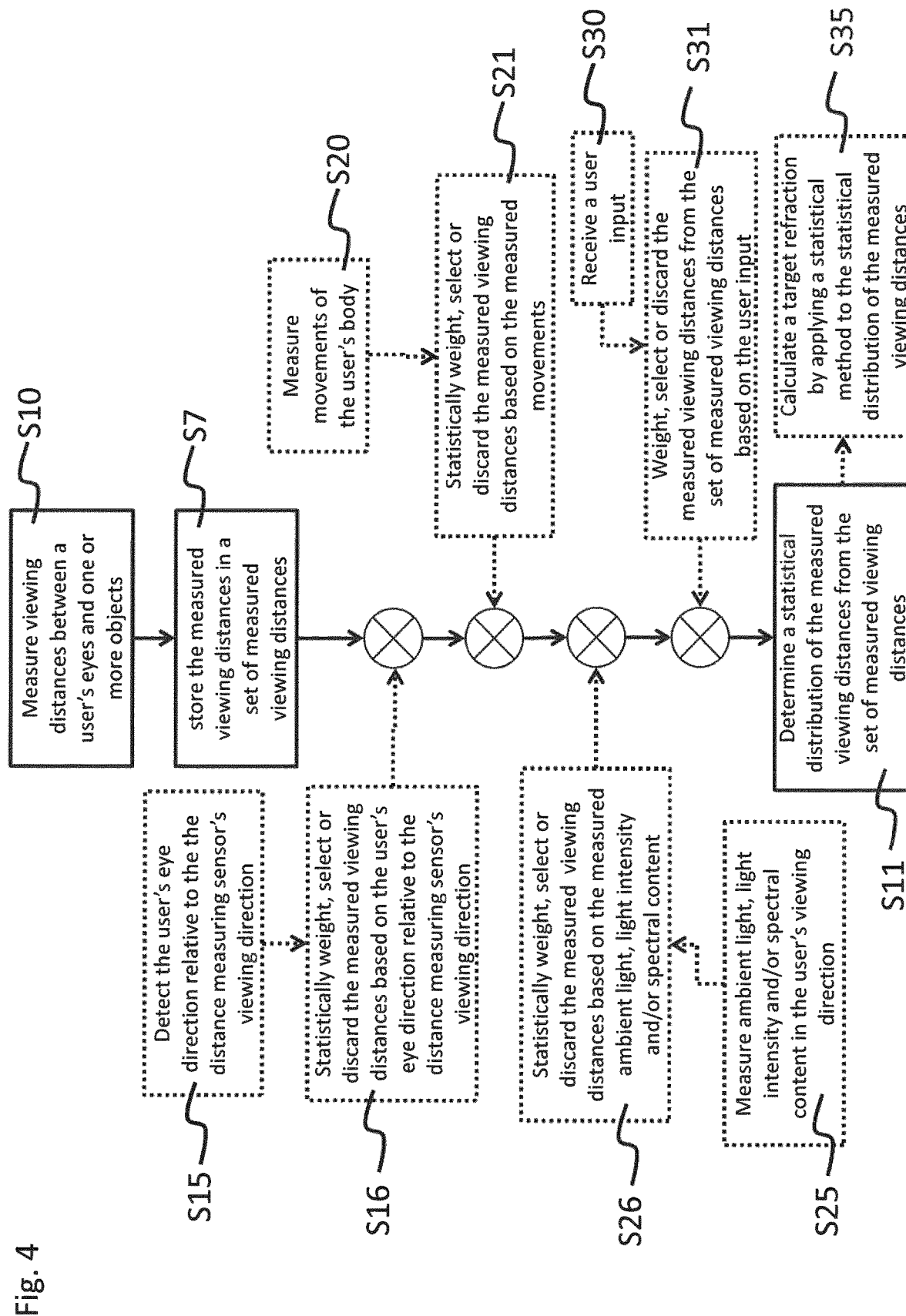
FIG. 4 illustrates a flow diagram corresponding to a method which may be performed by the distance sensing unit 110.

FIG. 4 illustrates a flow diagram corresponding to a method which may be performed by the distance sensing unit 110 in order to weight, prioritize or discard specific viewing distance measurements. The distance sensor 5 may measure one or more viewing distances in step S10. These distances are distances between a subject (i.e. user) and one or more objects in the subject's viewing direction. In step S7, the memory unit 7 may store the measured viewing distances in a set of measured viewing distances. In step S11, the processing unit 10 determines a statistical distribution of the measured viewing distances from the set of measured viewing distances.

In the following, some optional steps shown in FIG. 4 will be described. These optional steps usually lead to an improved, e.g. more precise, evaluation. For example, eye monitoring unit 15 detects, in optional step S15, the subject's eye direction relative to the distance measuring sensor's direction, e.g. viewing direction. In optional step S16, the processing unit 10 statistically weights, selects or discards the measured viewing distances from the set of measured viewing distances based on the subject's eye direction relative to the distance measuring sensor's direction, e.g. viewing direction. Instead of discarding the measured viewing distances, the processing unit 10 may select specific viewing distances regarded valuable or select a subject's preferred viewing distances or weight the measured viewing distances with a weighting factor smaller or greater than one. In optional step S20, a movement sensor 20 measures, in step S20, movements of the subject's body. In the present example, the movement sensor 20 may or may not comprise an accelerometer and/or a gyroscope, but may or may not further comprise different sensors like a magnetometer, an altimeter, a pedometer or a geopositioning device, for example. In optional step S21, the processing unit 10 statistically weights, selects or discards the measured viewing distances from the set of measured viewing distances based on the measured movements. If a subject's head is at least substantially steadily pointed to a measured object, the distance to the object is measured and weighted by a factor of one or higher than one. If the subject's attention is distracted, e.g. when a subject's head is moving at least substantially constantly around an object, the measured distance is weighted by a factor smaller than 1 or discarded and therefore not considered in the overall statistical distribution.

Ambient light sensor 25, which may be extended by using an additional color sensor, measures ambient light and/or light intensity and/or spectral content in the subject's viewing direction in optional step S25. The processing unit 10 statistically weights, selects or discards the measured viewing distances from the set of measured viewing distances based on the measured ambient light, light intensity and/or spectral content in optional step S26. The ambient light affects the subject's eye accommodation and depth-of-focus. Under bright illumination, when the pupil of the subject is constricted and subject's depth-of-focus is significantly increased, the measured viewing distances are deprioritized and weighted by values lower than one. When considering dim light, for example when the subject is reading a book and the subject's pupils are dilated, which corresponds to ambient light associated with dim illumination, the measured viewing distances are prioritized and weighted by values higher than one.

In optional step S30, a user interface 30 receives a user input. In optional step S31, the processing unit 10 weights, selects or discards the measured viewing distances from the set of measured viewing distances based on the user input. The subject may use a tap on the distance sensing unit 110, on attached devices or on glasses which comprise the distance sensing unit 110, in order to weight, select or discard the measured viewing distances. The subject's input can further be head gestures like nodding or shaking, detected by head motion sensor, subject or eye movement, detected by the eye monitoring device, and the like. For example, a subject might discard measured viewing distances by looking aside from the object to be measured, directly leading to discarded measuring results, because of the so adjusted eye monitoring device. Another example might be a subject putting his or her hands in front of the sensor with a waving hand gesture or keeping his or her hand in front of the distance sensing unit 110 for a few seconds to discard or weight measured viewing distances.

One or more, e.g. all of the aforementioned weighting or discarding steps may be performed independently from each other or together in a common processing step.

The processing unit 10 may calculate, in optional step S35, a target refraction by applying a statistical method to the statistical distribution of the measured viewing distances from the set of measured viewing distances.

Figure 5:
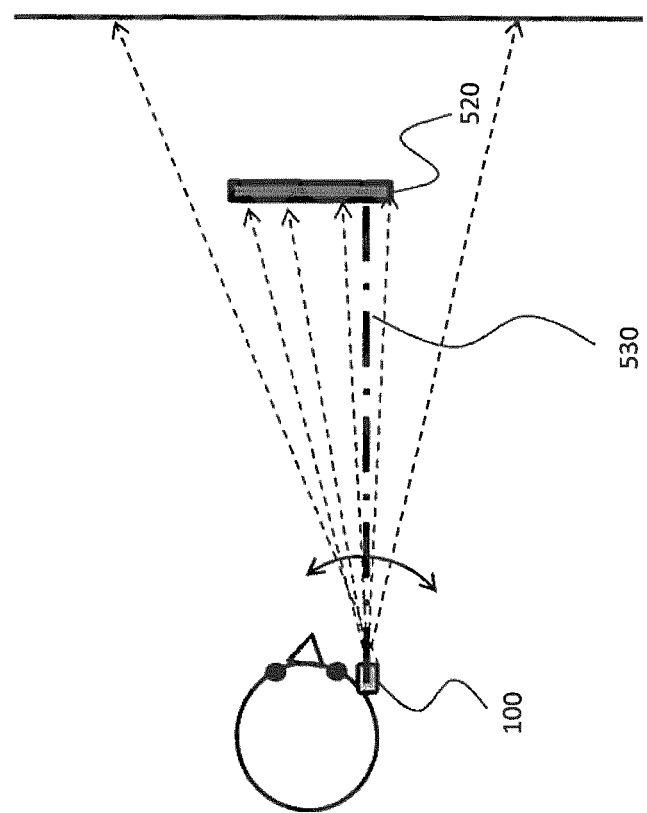
FIG. 5 illustrates a concept for passive scanning of an object.
Figure 5:
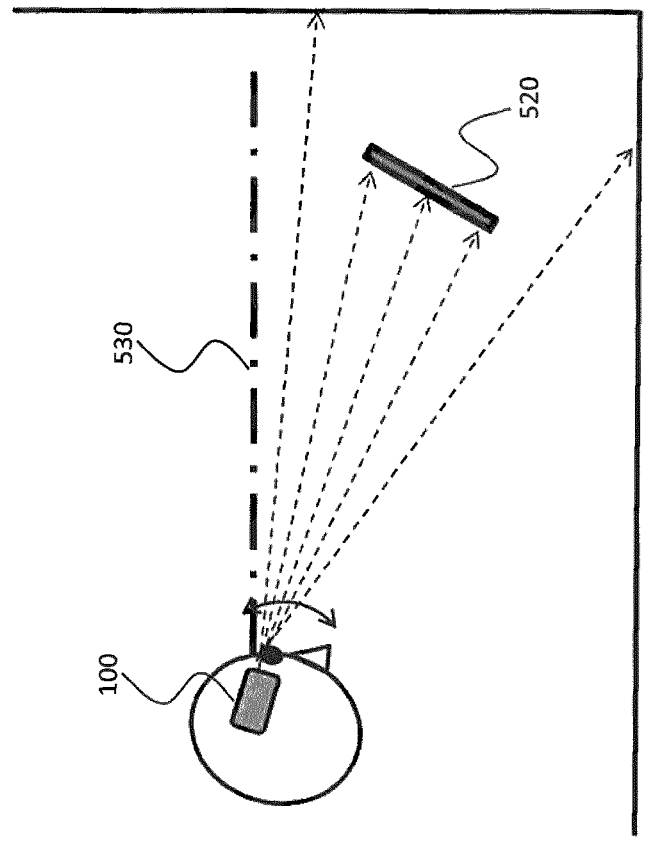

FIG. 5 illustrates a concept for passive scanning of an object. In the figure, the concept of scanning an object 520 or an environment (i.e. scene) with the distance sensing unit 110 using natural movements of a human body or a part of the body, such as a head (where the device is located) is depicted. For the passive scanning of the object (or scene), measurements from the orientation sensing unit 120 and/or the position sensing unit 150 may be used in addition to the measurements from the distance sensing unit 110. Optionally, motion sensors such as accelerometers, gyroscopes and magnetometers as well as location sensors may be implemented inside or outside of the orientation sensing unit 120. The position sensing unit 150 may be realised as at least one of a geopositioning device, indoor and an hybrid positioning system. The orientation sensing unit 120 may measure orientations vertically and/or horizontally relative to a base line 530 at an origin point.

In the figure, a user reading a book is exemplified. FIG. 5(a) illustrates measuring distances to a plurality of points of an object 520 and vertical orientations to the plurality of points relative to the base line 530. FIG. 5(b) illustrates measuring distances to the plurality of points of the object 520 and horizontal orientations to the plurality of points relative to the base line 530.

Since the passive scanning device 100 is equipped at the head of the user, the natural movement of the head during reading exposes sensor to various points and object 520 of the scene. Measured distances are recorded along with orientations and/or positions of the sensor 100. For example, when the user reads a book, he/she typically and slightly moves (rotates) the head to follow text and pages. The distances to different points of the book may be estimated by the distance sensing unit in the passive scanning device 100. As shown in FIG. 5(a), vertical orientations (angles) of each of the distances may be estimated by the orientation sensing unit 120. For example, the vertical orientations may be estimated using an accelerometer which may measure angles in relation to the gravitational field. In FIG. 5(b), horizontal orientations (angles) of each of the distances may be estimated by the orientation sensing unit 120. For example, the horizontal orientations may be measured using a magnetometer (or a compass) which may measure angles in relation to a direction of the earth magnetic field. By combining measurements of the distances and orientations, the scanned points of the book can be located in 3D space (relative to the user or the passive scanning device). The located points in 3D space (coordinates) may provide information about a shape of the book, angles (inclinations) of the book, a distance to the book and/or a size of the book. From this information, it is possible to relate distance measurements to the physical world such that the measured data is used to characterize or classify an object of interest or an activity of the user, e.g. the interest in or activity of reading a book. By knowing position of device 100 in relation to user eyes it is possible to estimate viewing distance to the object 520. Position of the device 100 in relation to user eyes can be known due to predefined wearing conditions or from calibration data.

The points to the objects (e.g. wall) which are not of the direct interest to the user for classified activity are not considered for the estimation of viewing distance to the object of primary interest (e.g. book). However, distances to the other objects can provide additional information about the scene. In the depicted figures, coordinate points measured due to the wall may be taken into account when the passive scanning device 100 classifies the scene. For example, together with the classified object (which may be a book in the figure) the coordinate points of the wall may lead the classification to the scene of the user reading the book indoors.

Figure 6:
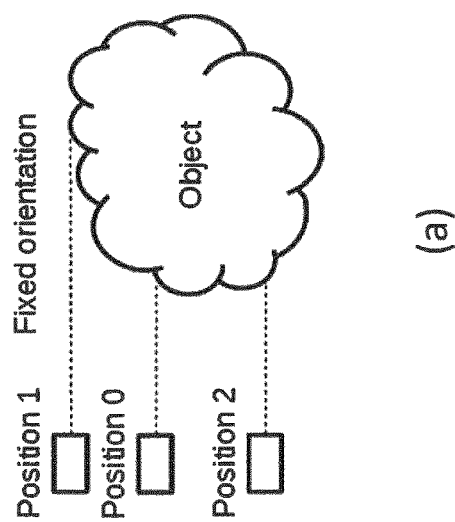
FIG. 6 illustrates examples of passive scanning by measuring orientations and/or positions of an object.
Figure 6:
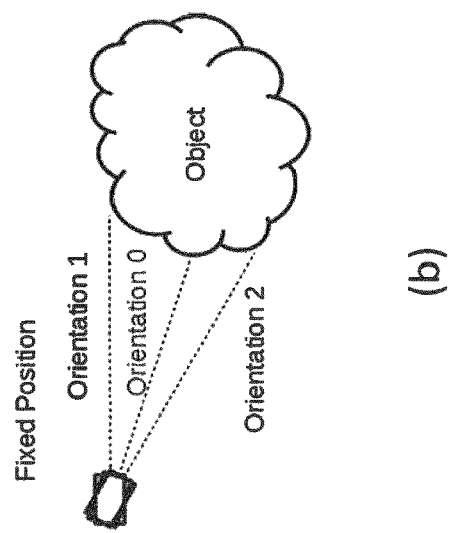
Figure 6:
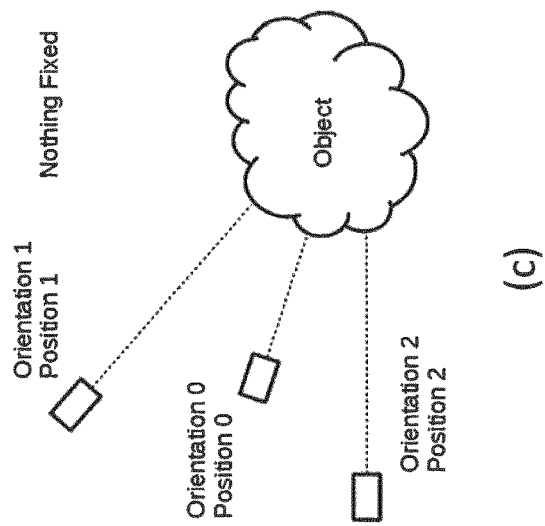

FIG. 6 illustrates examples of passive scanning by measuring orientations and/or positions of an object. In order to obtain a scan of the object one needs to measure a property of the object (surface) in relation to a position on the object (surface). If the geometry of an object is scanned, distances to the object are related to the coordinate system of the object and/or measuring device. In 3D space, orientations and/or positions of the passive scanning device 100 or the distance sensing unit 110 in relation to the object (e.g., scene) may needed to be measured to passively scan the objet.

Referring to FIG. 6(a), when the direction (i.e. orientation) of the distance sensing unit 110 is restricted (or assumed to remain constant), the object can be scanned by measuring positions (e.g. positions 0, 1, 2) of the distance sensing unit 110. As depicted, points of the object may be measured by the distance sensing unit 110 and the position sensing unit 150. The measured points may be plotted in the coordinate systems.

Referring to FIG. 6(b), when the position of the distance sensing unit 110 is restricted (or assumed to remain constant), the object can be scanned by measuring orientations (e.g. orientations 0, 1, 2) of the distance sensing unit 110. This is the most natural situation for the device which is mounted on the user head for many visual activities, since humans tend to rotate the head in order to study the scene. As depicted, points of the object may be measured by the distance sensing unit 110 and the orientation sensing unit 120. The measured points may be plotted in the coordinate systems.

Referring to FIG. 6(c), when the position and orientation of the distance sensing unit 110 are restricted (or assumed to remain constant), the object can be scanned by measuring orientations (e.g. orientations 0, 1, 2) and positions (e.g. positions 0, 1, 2) of the distance sensing unit 110. As depicted, points of the object may be measured by the distance sensing unit 110, the orientation sensing unit 120 and the position sensing unit 150. The measured points may be plotted in the coordinate systems.

As shown, at any condition of the restrictions for the orientation and/or position of the passive scanning device 100 or the distance sensing unit 110, monitoring or scanning of the object, e.g. scene, is still feasible. That is, active controls of the sensors for monitoring the object or scene can be omitted.

Orientations can be monitored with inertia sensors (e.g. an accelerometer gives a direction to the earth's gravitation field, i.e. vertical angle, a magnetometer gives a direction to the earth's magnetic field, mostly horizontal angle, as well as partly vertical). During the measurements for the orientations, a gyroscope may be used to reduce artefacts. Measurements of multiple motion sensors can be combined with the help of so-called fusion algorithm in order to improve accuracy. Positions can be derived from direct measurements, like at least a single coordinate from geolocation, indoor location, or altimeter or can be derived indirectly by sensing the sensor motion and performing position estimation from motion (dead reckoning/path integration).

The object light reflection properties, including spectral information on the reflection as additional information may be also measured and used for object recognition (passive scanning of the object).

Figure 7:
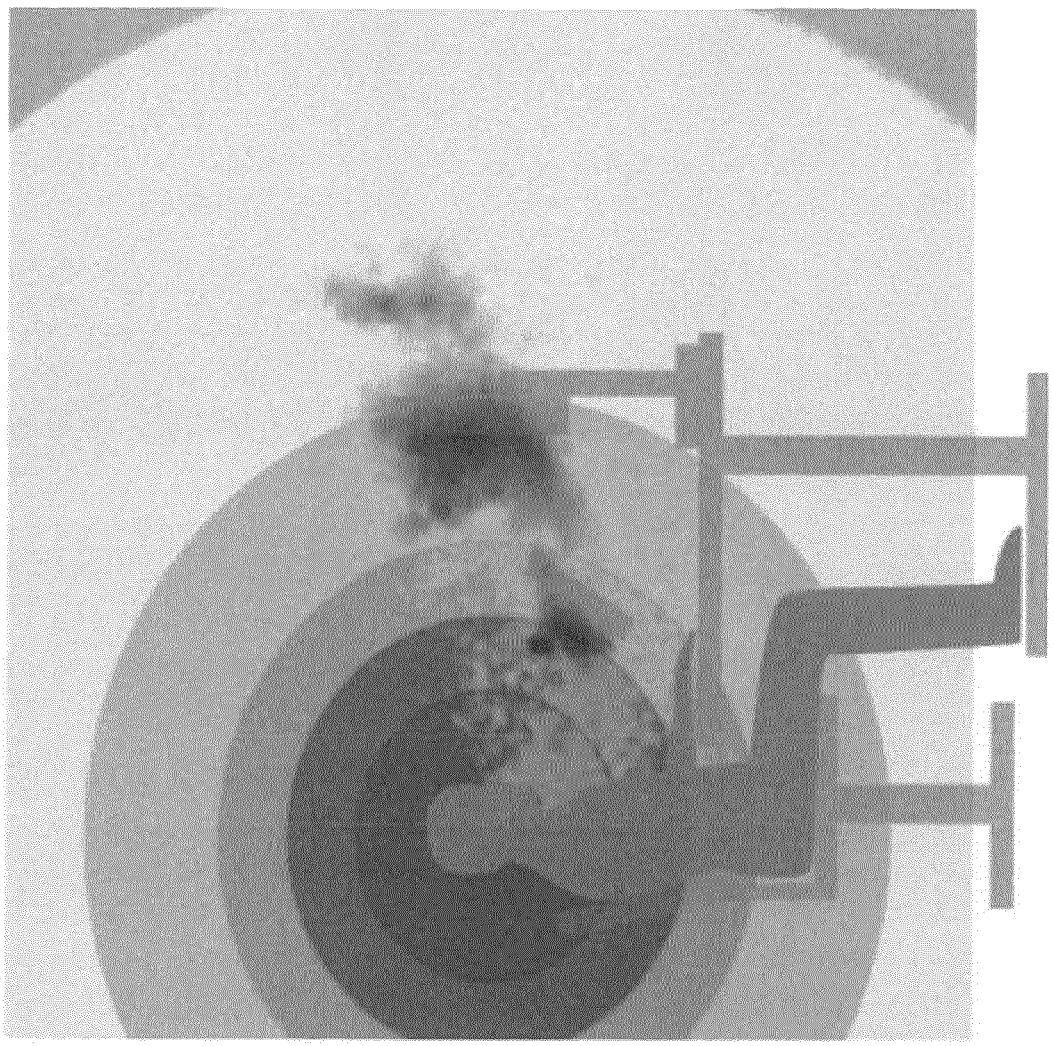
FIG. 7 illustrates examples of plotting points (or points cloud) of the measured data for objects or scenes.

FIG. 7 illustrates examples of plotting points (or points cloud) of the measured data for objects or scenes. In the figure, points derived from the measured data including the distances and the orientations (and/or positions) are plotted in 2-dimensional coordinates of the vertical cross cut of the scene. The points are mapped based on distance measurements combined with orientation of gravitational field measured with accelerometer. The figure shows results of the plotted points for activities using a tablet and a desktop computer. For the activity of using the tablet computer, the plotted points reflect an inclination of a screen of the tablet computer and a distance from the user. The plotted points for the activity of the user using the desktop computer reflect a vertically standing computer monitor and relatively long distance from/to the user.

In the figure, insignificant plotted points are also presented as being pale and semi-transparent whereas significant plotted points are presented as being vivid. That is, depending on a frequency of occurrences of the plotted points, color of the plotted points may be pale or vivid. To simplify the passive scanning, the significant plotted points may be taken into account for the classification of the object or the environment whereas the insignificant plotted points can be disregarded for the classification. For example, if the frequency of plotted points in a predetermined area in the coordinates is less than the average of frequencies of plotted points in other areas, the plotted points in the predetermined area can be excluded from consideration for the classification.

According to the present disclosure, once the object or objects composing the scene are modeled and/or classified, the activity of the user, such as reading a book, using a smartphone, using a PC, watching TV, talking to other people, etc., can be classified as well.

Figure 8:
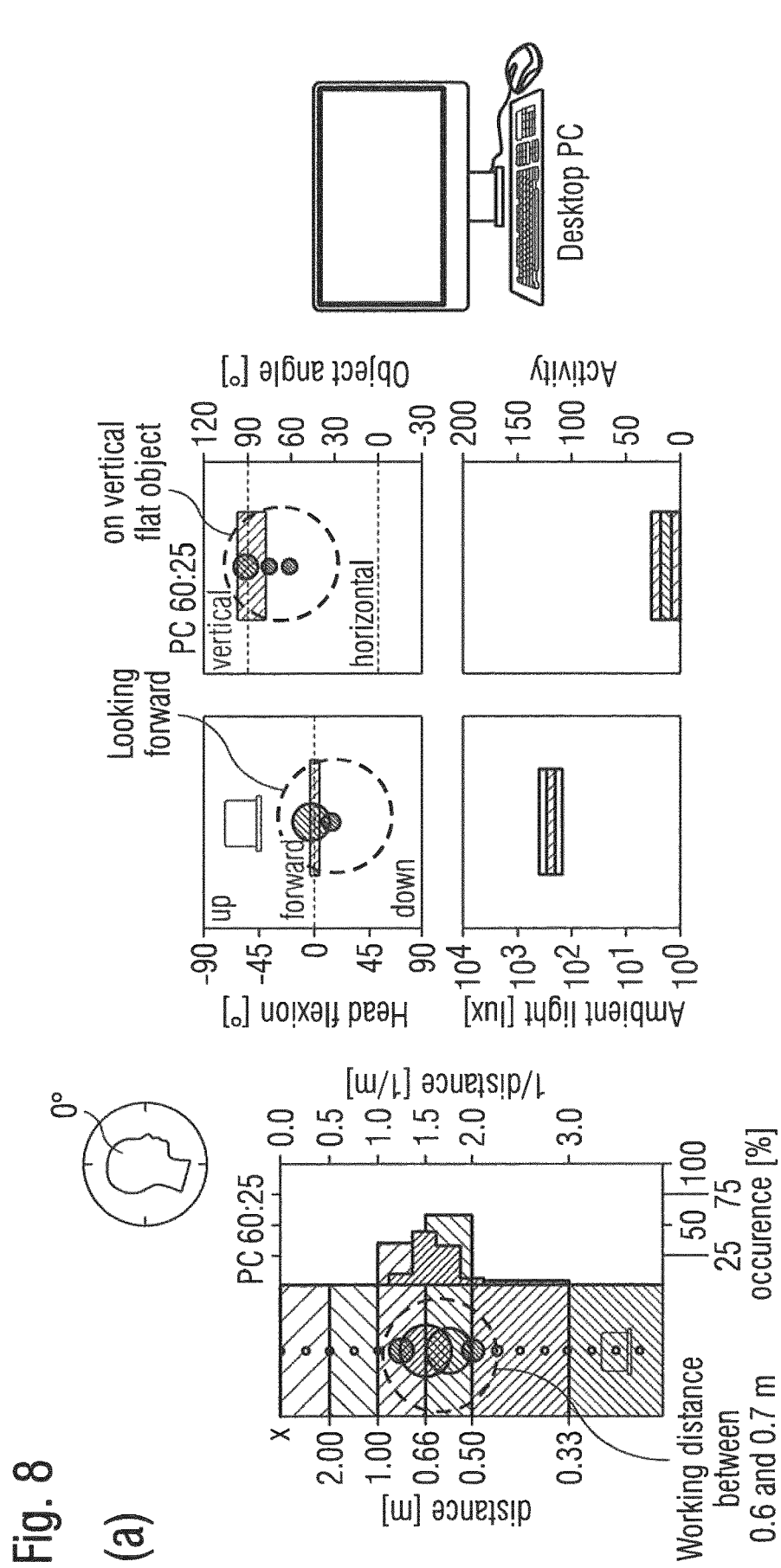
FIG. 8 illustrates an example of measurements for a user activity of utilizing a desktop personal computer.
Figure 8:
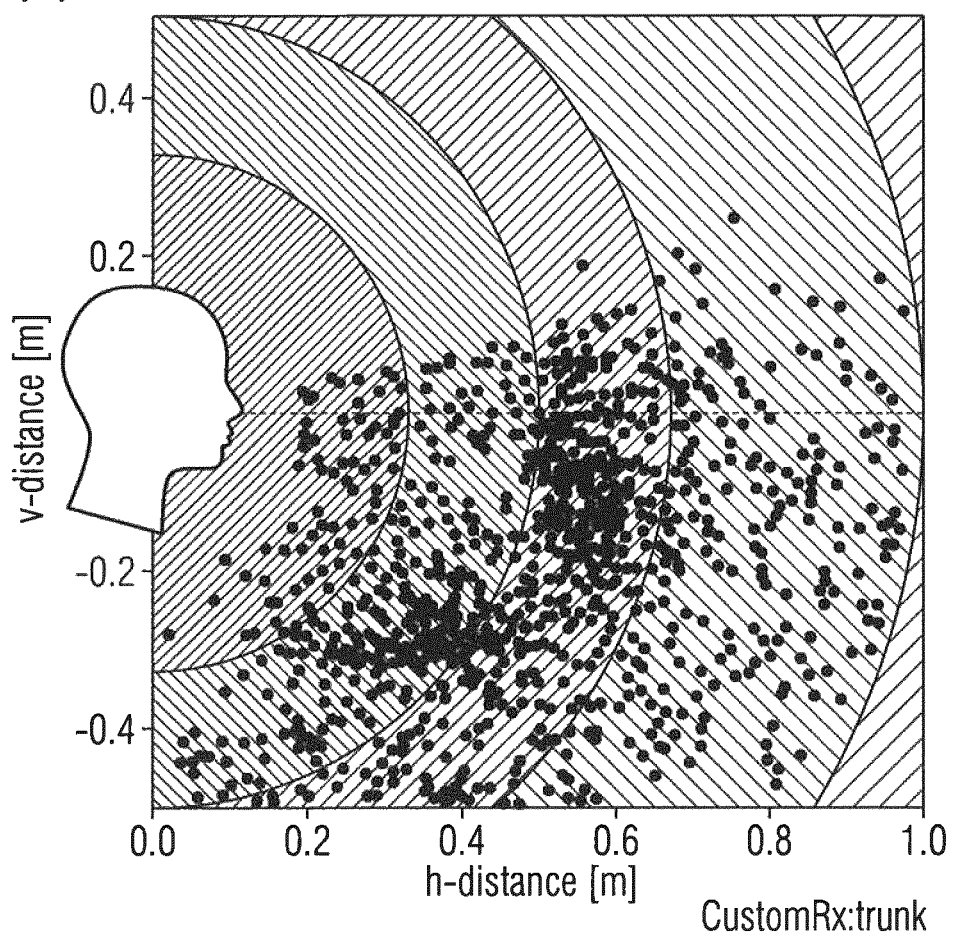

FIG. 8 illustrates an example of measurements for a user activity of utilizing a desktop personal computer. FIG. 8(a) illustrates results of various measurements which may be performed in the passive scanning device. FIG. 8(b) illustrates points cloud (or plotted points) in 2-dimensional coordinates by reflecting the measured distances and the measured vertical orientations for the points of the desktop PC.

Referring to FIG. 8(a), distances and occurrences of each of the distances can be measured by the passive scanning device 100. Since the occurrences for the distances between 0.6 m and 0.7 m make up a significant percentage in measured distances, the distance between 0.6 m and 0.7 m can be determined as the working distance (distance between the user and the object of interest) of the object. Vertical orientations for the distances making up a significant percentage may be measured and indicate that the user mostly looked forward during the measurements. The combinations of the vertical orientations and the distances making up a significant percentage may also indicate an inclination of the object. The example depicted in this figure shows that the object is vertically flat. Ambient light in the environment where the object is located and an amount of head movement may be measured and be taken into account to classify the object (or scene) and the activity of the user.

Referring to FIG. 8(b), points based on the measured data are plotted in 2-dimensional vertical cross cut of the scene, similar to FIG. 7. The x-axis denotes the horizontal coordinates of the points of the object and the y-axis denotes the vertical coordinates. The plotted points indicate a computer monitor standing vertically and a keyboard on a desk.

Figure 9:
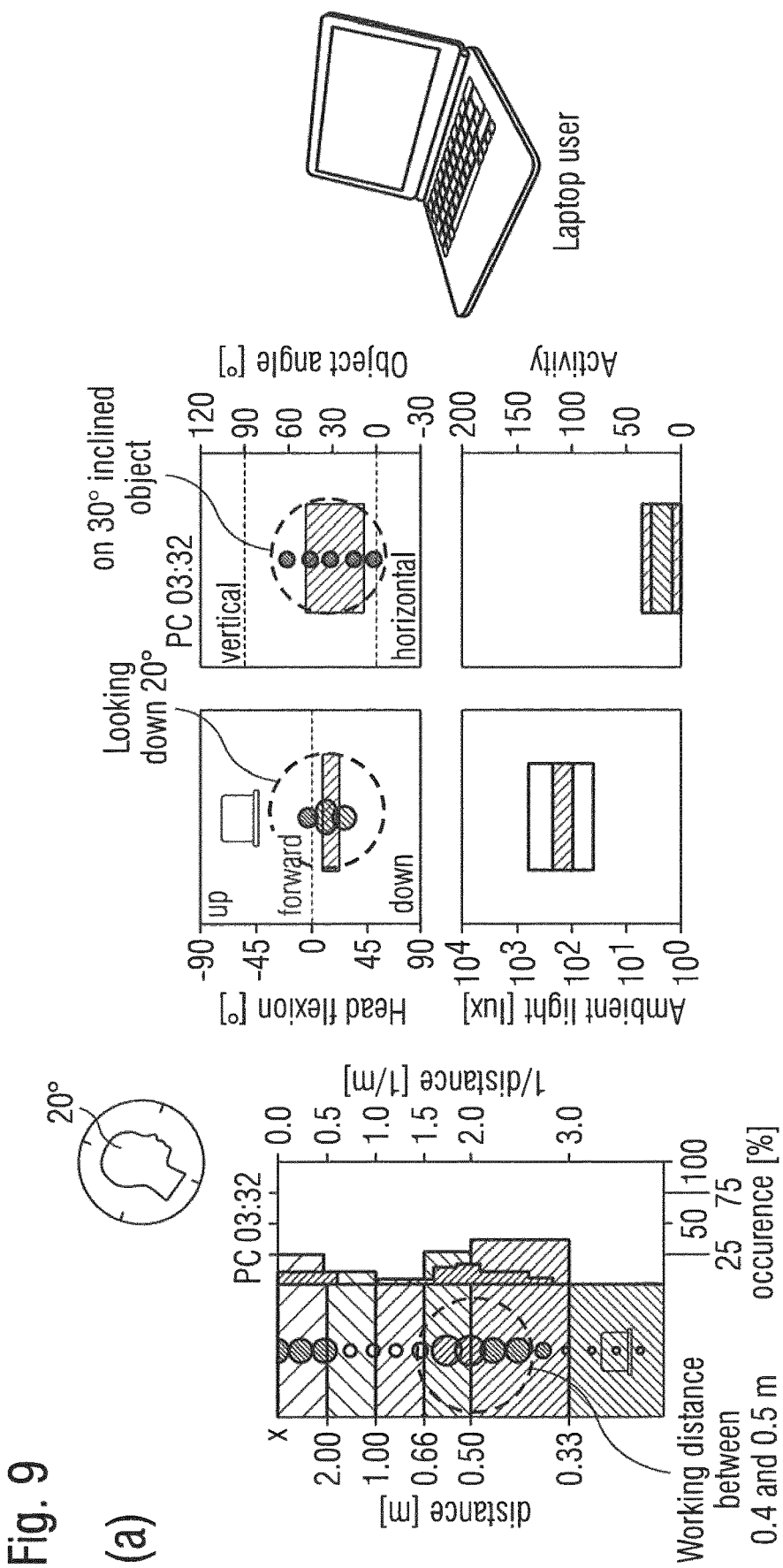
FIG. 9 illustrates an example of measurements for a user activity of utilizing a laptop computer.
Figure 9:
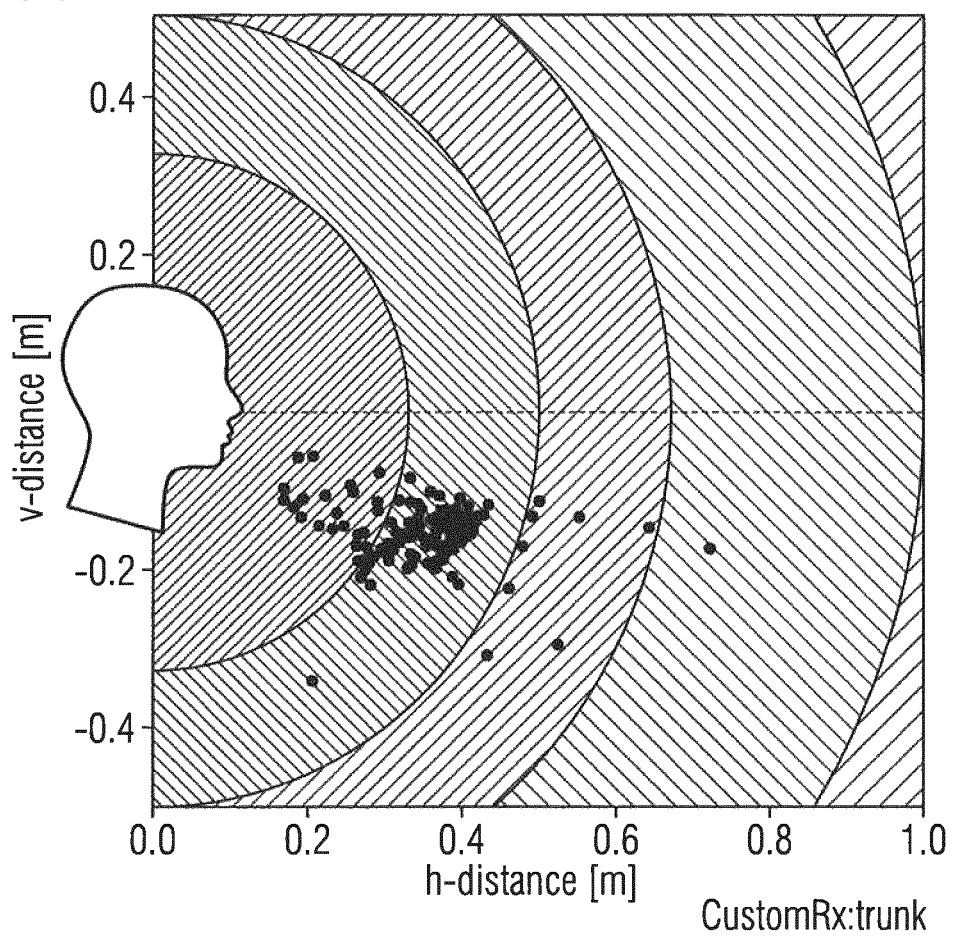

FIG. 9 illustrates an example of measurements for a user activity of utilizing a laptop computer. Meaning of the plots is similar to FIG. 8. FIG. 9(a) illustrates results of various measurements which may be performed in the passive scanning device 100. FIG. 9(b) illustrates plotted points in 2-dimensional coordinates by reflecting the measured distances and the measured vertical orientations for the points of the laptop computer.

Referring to FIG. 9(a), distances and occurrences of each of distances can be measured by the passive scanning device 100. Since the occurrences for the distances between 0.4 m and 0.5 m make up a significant percentage in the measured distances, the distance between 0.4 m and 0.5 m can be determined as the working distance (distance between the user and the object of interest). Head flexion angles (device pitch) may be measured and indicate that the user mostly looked 20 degrees down during the measurements. The combinations of the vertical orientations and the distances making up a significant percentage may also indicate an inclination of the object. The example depicted in this figure shows that a part of the object is inclined about 30 degrees. Ambient light in the environment where the object is located and an amount of head movement may be measured and be taken into account to classify the object and the activity of the user.

Referring to FIG. 9(b), points based on the measured data are plotted in 2-dimensional coordinate system of device. The x-axis denotes the horizontal coordinates of the points of the object and the y-axis denotes the vertical coordinates. The plotted points indicate an inclined surface such as a book or a screen of a laptop computer.

Figure 10:
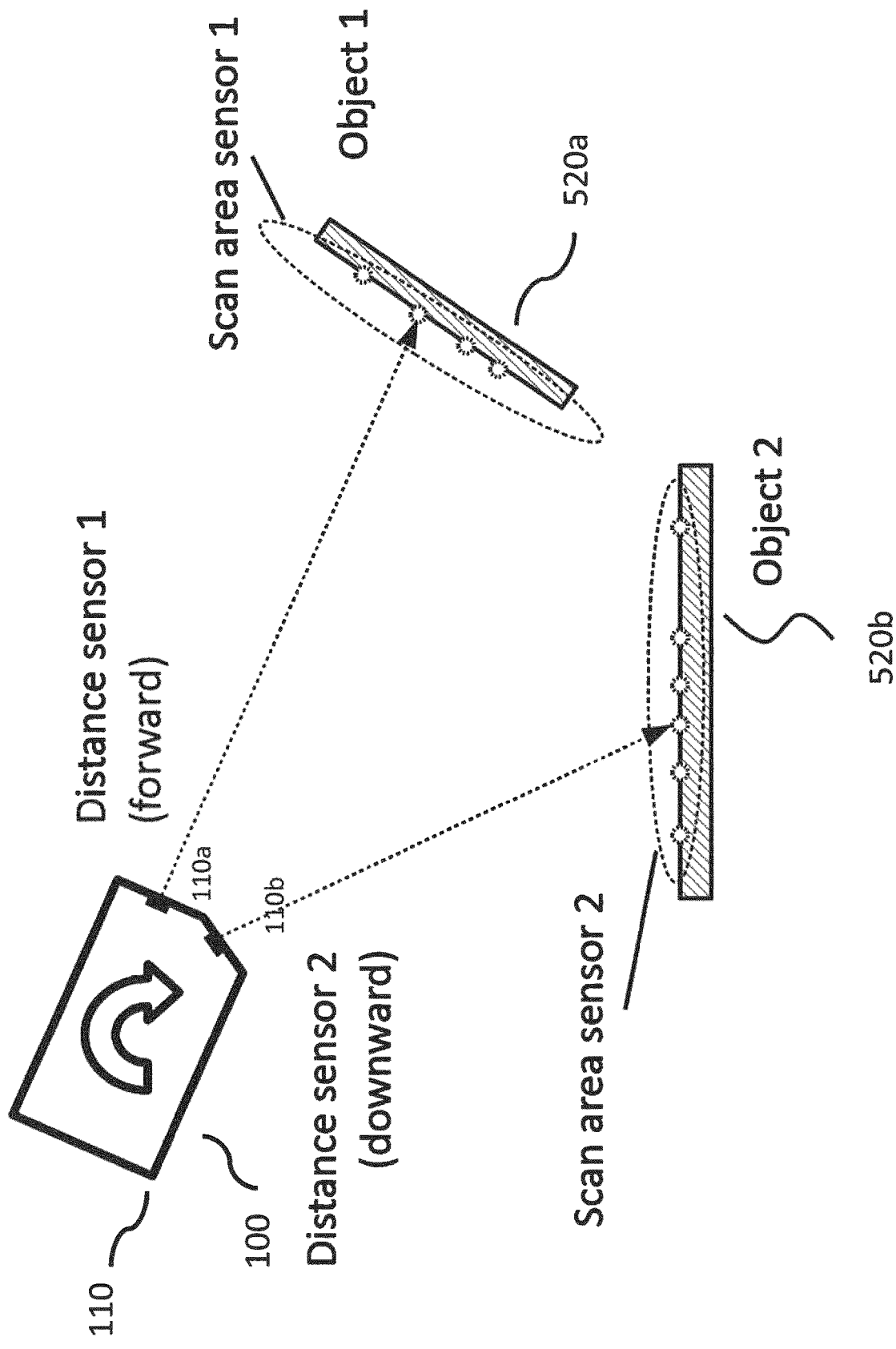
FIG. 10 illustrates an example of passive scanning of objects using a plurality of distance sensors included in the distance sensing unit 110.

FIG. 10 illustrates an example of passive scanning of objects using a plurality (two in this example) of distance sensors included in the distance sensing unit 110. The distance sensing unit 110 can be composed of a single-sensor or a sensor array for performing multiple measurements at the same time. The sensor array may include or be formed by a plurality of distance sensors. For example, the sensor array may be realised by the laser-based Time of Flight (ToF) sensors, which have nine zones for ranging. The sensor array's measurements may be combined to reinforce information about an environment where the passive scanning device 100 is located. The distance sensing unit 110 may use laser-based technology, ultrasound-based technology or any other ranging technology. The distance sensing unit 110 can even be a 3D camera. Range measurements performed by the distance sensing unit 110 can be related to orientations/positions measurements performed by the orientation sensing unit 120 that may include the motion sensor or position sensor.

Referring to the figure, the passive scanning device 100 exemplarily comprises two distance sensors. The first distance sensor 110a may be configured and arranged to measure distances in the forward direction of the device 100 so that the distances measured by the first distance sensor 110*a* may correspond to distances between the user and the object. Since a first object 520*a* is located on the line of sight of the user, the first distance sensor 110*a* may measure distances from the device 100 (or user) to points of the first object 520*a*. The second distance sensor 110*b* may be implemented and arranged to measure distances of a slightly downward direction of the device 100 so that a second object 520*b* which is not exactly on the line of sight of the user can be measured by the second distance sensor 110*b*. For example, the user using a laptop computer normally mostly looks at the screen. So, the distance sensing unit 110 of the passive scanning device 100 may mainly measure distances to the screen of the laptop computer which may result in points cloud (or plotted points) having a contour of the inclined screen. The laptop computer may also have a keyboard portion, however, the distances to the keyboard may only be measured occasionally by the distance sensor 110, since the user may look down for a few times. Thus, it is likely that the data measured by the distance sensor 110 is ignored since the distances to second object 520*b* are insignificant. In this case, the second distance sensor 110*b* may measure distances to points of the keyboard of the laptop computer even though the user's attention is mainly drawn to the screen of the laptop computer. As a consequence, the passive scanning device 100 comprising a plurality of distance sensors 110*a*, 110*b* is able to measure objects located in the environment or around the user so that more precise results for modelling and classifying the scene (or object) or the activity of the user can be achieved.

Figure 11:
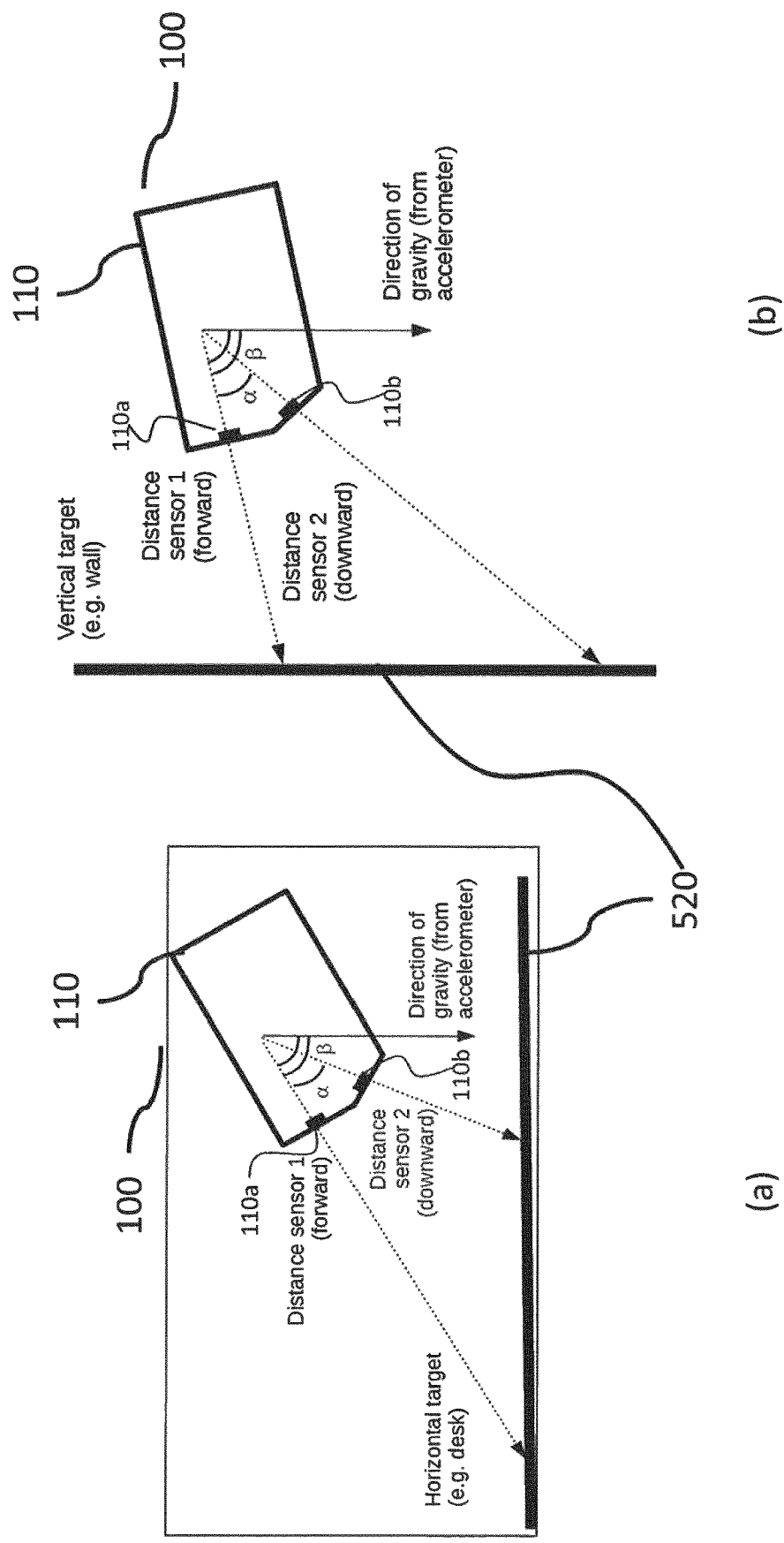
FIG. 11 illustrates an example of passive scanning of an object 520 using a plurality of distance sensors 110a, 110b.

FIG. 11 illustrates an example of passive scanning of an object 520 using a plurality of distance sensors 110*a*, 110*b*. The distance sensing unit 110 comprising more than one distance sensor can be beneficial when the object to be scanned (measured) is relatively big in size. Referring to the figure, the first distance sensor 110*a* for measuring the forward direction distances may measure points of the object 520 where the user's gaze is. At the same time, the second distance sensor 110*b* for measuring the slightly downward direction distances may measure the other points of the object 520. By simple geometrical evaluation it is possible, for example, to calculate angle of the objects/surfaces shown on the image. Consequently, the passive scanning device 100 having more than one distance sensor is able to enhance accuracy and speed of the passive scanning, modeling and classification of the object 520 (or scene).

FIG. 11(*a*) illustrates an example of scanning of the surface (of the horizontal object) by using the passive scanning device 100 or the distance sensing unit 110 having the plurality of distance sensors 110*a* and 110*b*. FIG. 11(*b*) illustrates an example of scanning of the surface (of the vertical object) by using the passive scanning device 100 or the distance sensing unit 110 having the plurality of distance sensors 110*a* and 110*b*.

Figure 12:
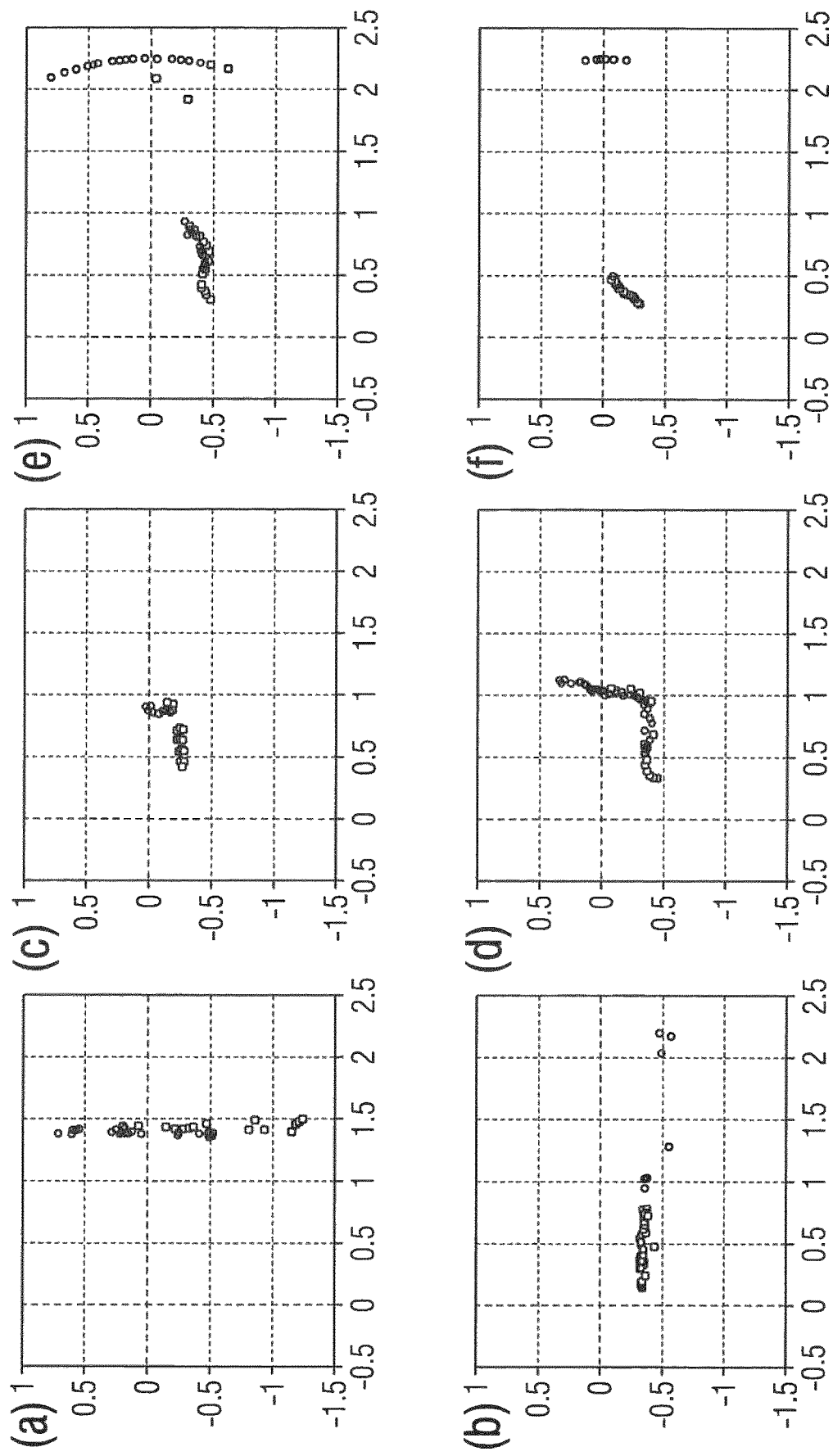
FIG. 12 illustrates examples of mappings of objects (surfaces of the objects) obtained with passive scanning with wearable device mounted on the spectacles temple by combining the measurements of the distances and the orientations (and/or positions) from the passive scanning device 100.

FIG. 12 illustrates examples of mappings of objects (surfaces of the objects) obtained with passive scanning with wearable device mounted on the spectacles temple by combining the measurements of the distances and the orientations (and/or positions) from the passive scanning device 100. Horizontal dimensions in the figure denote horizontal distances in meters and vertical dimensions denote vertical distances in meters. Centre on the cross of dashed lines is a location of the passive scanning device 100 or the distance sensing unit 110. Black lined circles show the measurements of TOF of the distance sensors 110*a* and circles without lines show the measurements of TOF of the distance sensors 110*b*.

In many applications it is important to be able to understand visual requirements of the user. For example, to better design spectacle or intraocular lenses one has to understand user's visual lifestyle: how much time user spends reading, watching TV, working on the computer, etc. What are the typical viewing distances to the objects of interest of such activities? Visual behaviour can be studied using highly portable unobtrusive wearable devices which are mounted in the proximity of the user eyes and are able to scan the scene as viewed by the user in order to derive statistics of viewing distances, times, conditions as well as additional information about user movements, ambient light, colour, etc. Such information can be collected continuously during user daily activities and being analysed in a specific manner can be used to design individualized visual solutions, such as ophthalmic and intraocular lenses, refractive treatments, etc.

The apparatus and device described herein facilitate an efficient way of collecting and evaluating such information.

Referring to FIG. 11(*a*), mappings of the measurements for a vertical surface (e.g. a wall) are depicted. Referring to FIG. 11(*b*), mappings of the measurements for a horizontal surface (e.g. a desk) are depicted.

Referring to FIG. 11(*c*), mappings of the measurements for a desktop computer at an office are depicted. Referring to FIG. 11(*d*), mappings of the measurements for a desktop computer with the screen close to the wall are depicted. In the FIG. 11(*d*), a wall behind a monitor of the desktop computer is also scanned.

Referring to FIG. 11(*e*), mappings of the measurements for a laptop computer are depicted. Referring to FIG. 11(*f*), mappings of the measurements for a book are depicted.

Figure 13:
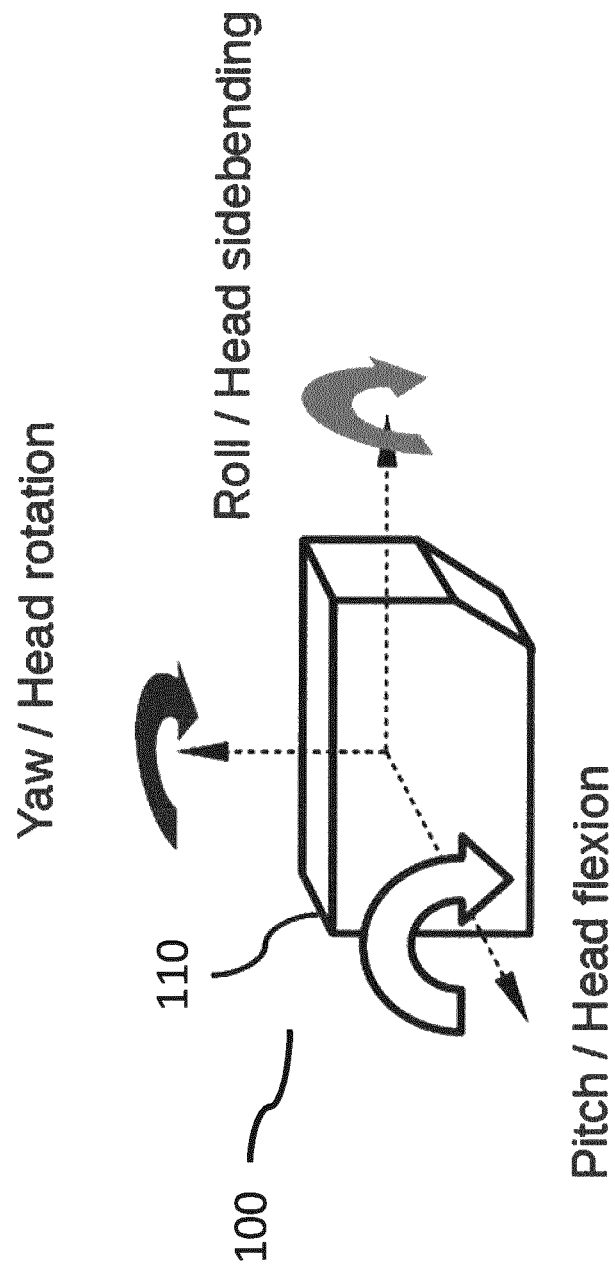
FIG. 13 illustrates types of the orientations of the passive scanning device 100 or the distance sensing unit 110 that may be measured by the passive scanning device 100 or the orientation sensing unit 120.

FIG. 13 illustrates types of the orientations of the passive scanning device 100 or the distance sensing unit 110 that may be measured by the passive scanning device 100 or the orientation sensing unit 120. Yaw orientation (rotation) may be defined as rotation around the vertical axis and reflect head rotation when the passive scanning device 100 is mounted on the head of the user. Pitch orientation (rotation) may be defined as rotation around the pitch axis and reflect head flexion when the passive scanning device 100 is mounted on the head of the user. The pitch axis may be defined as its origin at the center of gravity and is directed to the right, parallel to a line drawn from side of the passive scanning device 100. Roll orientation (rotation) may be defined as rotation around the roll axis and reflect head side bending when the passive scanning device 100 is mounted on the head of the user. The roll axis may be defined has its origin at the center of gravity and is directed forward, parallel to the passive scanning device 100.

Figure 14:
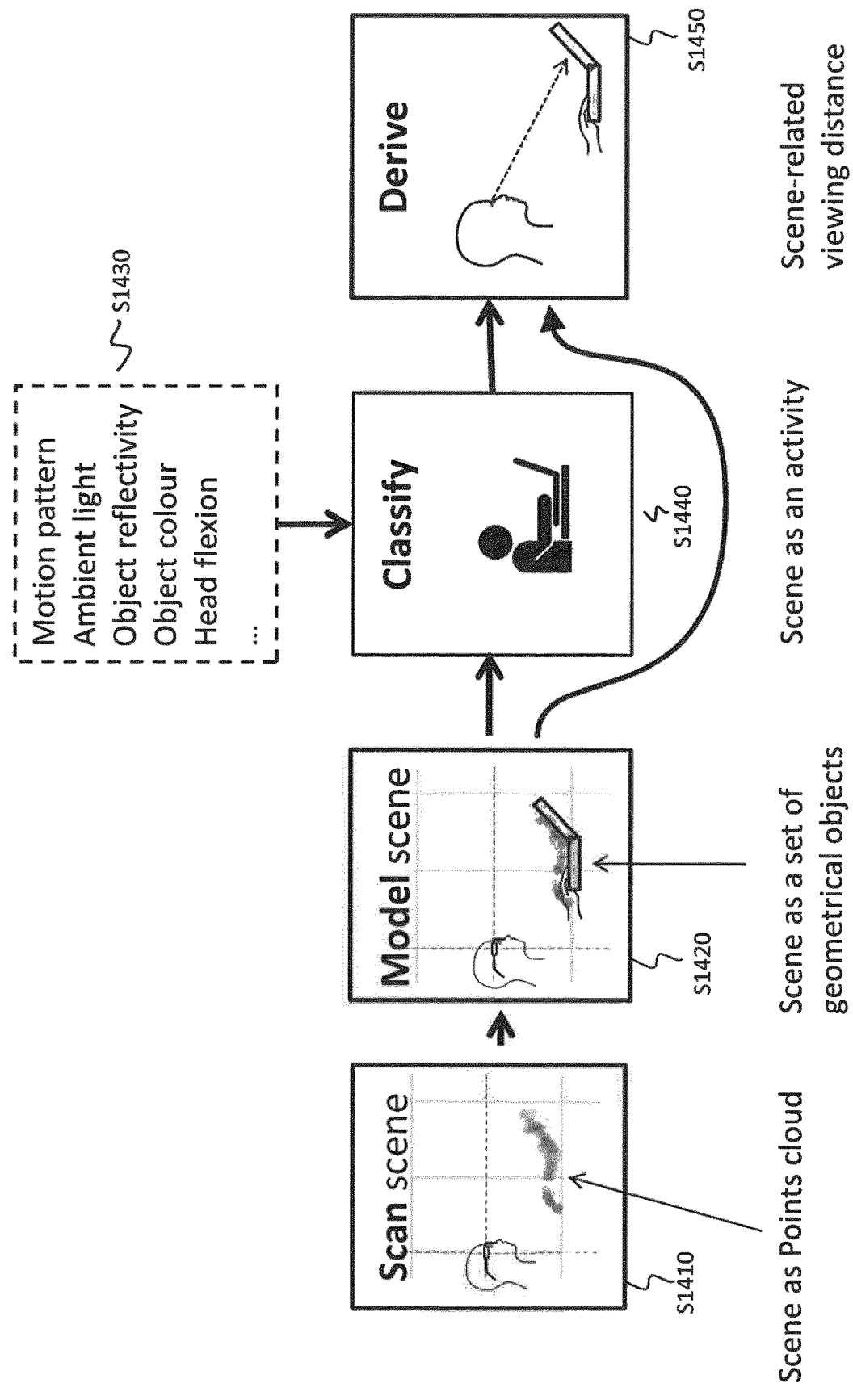
FIG. 14 illustrates an example flow for classifying the object or scene.

FIG. 14 illustrates an example flow for classifying the object or scene.

The points cloud may be measured by the passive scanning device 100 or derived from the measurements of the passive scanning device 100 (S1410). The measurements may include distances to one or more objects in a scene and orientations (and/or positions) of the passive scanning device 100 (or the distance sensing unit 110). The measurements may be converted to the point cloud in the coordinate system related to the one or more objects.

The points cloud may be converted to model composed of geometrical primitives (S1420). The geometrical primitives may indicate surfaces of the one or more objects in the scene.

In the scene the one or more objects may be identified and then the scene can be classified based on the identified one or more objects (S1440). The scene may be defined as an activity of the user and/or an environment of the user.

Optionally, information on at least one of motion pattern, ambient light, object reflectivity, object contour, object colour or head flexion can be further measured by the passive scanning device 100 or auxiliary equipments connected to the passive scanning device 100 (S1430). Then the information may be taken into account when the scene is classified (S1440).

Based on the geometrical primitives or the classified scene, information such as a working distance, a viewing distance and/or a working environment may be derived. The information may be calibrated with the statistical methods and be used to identify a refraction solution of the user (S1450).

Figure 15:
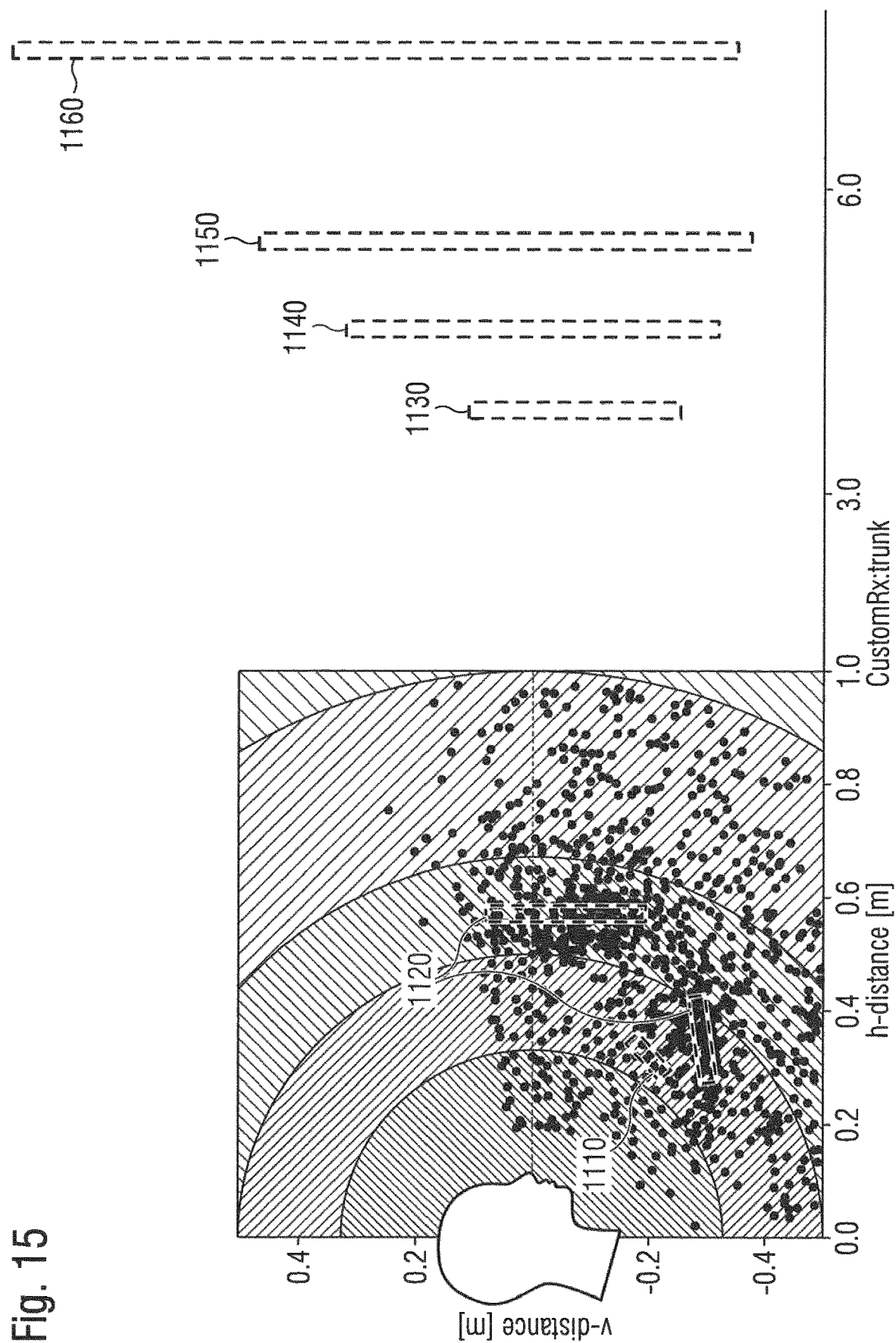
FIG. 15 illustrates examples of plotted points in 2-dimensional coordinates for reference data of example objects.

FIG. 15 illustrates examples of plotted points in 2-dimensional coordinates for reference data of example objects. The reference data may be defined for various types of example objects. In the figure, the reference data for the example objects are plotted in 2-dimensional coordinates. For example, in the figure, reference data for a book 1110, a desktop PC screen 1120, a 30-inch TV 1130, a 40-inch TV 1140, a 50-inch TV 1150 and a projection screen 1160 are plotted. Since the reference data may include reference distances, reference vertical orientations and reference vertical orientations, it is also possible that points for the reference data are plotted in 3-dimensional coordinates. In the figure, the reference data are, nevertheless, expressed in 2-dimensional coordinates for ease of presentation and explanation.

In the figure, the measured data are plotted at distances between 0.2 m and 0.6 m. The plotted points mostly match the reference data for the desktop PC 1120. Thus, the object measured by the passive scanning device 100 may be classified as a desktop PC.

A 3D object as perceived by the passive scanning device 100 may consists of a plurality of surfaces. As the position of the passive scanning device 100 changes around the 3D object, the surfaces of the 3D object may be scanned and the points of the surfaces may be measured. The measurements of the 3D object may include the points of the surfaces as well as mutual arrangements of the surfaces. In this case, the reference data may include examples for the object shapes of the surfaces and the mutual arrangements of the surfaces.

From the measurements of the passive scanning device 100, information about is object that constitutes of shapes of the objects, poses of the objects and/or positions of the object may be acquired. A model for a complex object can be composed of 3D primitives (rigid objects) and their spatial relationships. For example, if an object is a human body, the model may consist of primitives of a head, a torso, arms, legs, etc. The spatial relationships (degrees of freedom) are then defined by physiological restrictions. Such spatial relationships may be taken into account in the reference data. The derived information from human body as an object thus can be distance, pose, orientation and so on, and the corresponding data as the reference data may be stored in the memory unit 130.

Another example of a complex object could be a laptop computer. The laptop computer is typically composed of a rigid monitor and a rigid main body, which can have a variable angle between them, based on preferences of the user. In this case, a model can be representation with those two primitives (of the monitor and main body) and as single variable relationship of an angle. The derived information would be the size and aspect ratio of the monitor, angle between monitor and main body, as well as position and pose of the laptop.

The 3D Scene is composed of set of 3D objects (primitive or complex). The scene model consists of presences of the objects, shapes of the objects, poses of the objects and spatial relationships of the objects. Here, the term "pose" includes the object position and orientation. Thus the scene recognition requires recognition of set of composing objects and their arrangement in space.

The scene recognition further allows deriving activity of the user. For example, identifying a laptop within specific area of viewing space (within the arm reach), with a specific pose (a monitor turned towards user), in a specific condition (a laptop lid is open) may suggest that user is working on the laptop. In another example, presence of the object in near range (reading distance) around the head of the user, with a size of 20×30 cm, with rotations of the passive scanning device 100 in relatively limited range, may be identified the object as a book and the scene (or activity) as reading activity.

Figure 16:
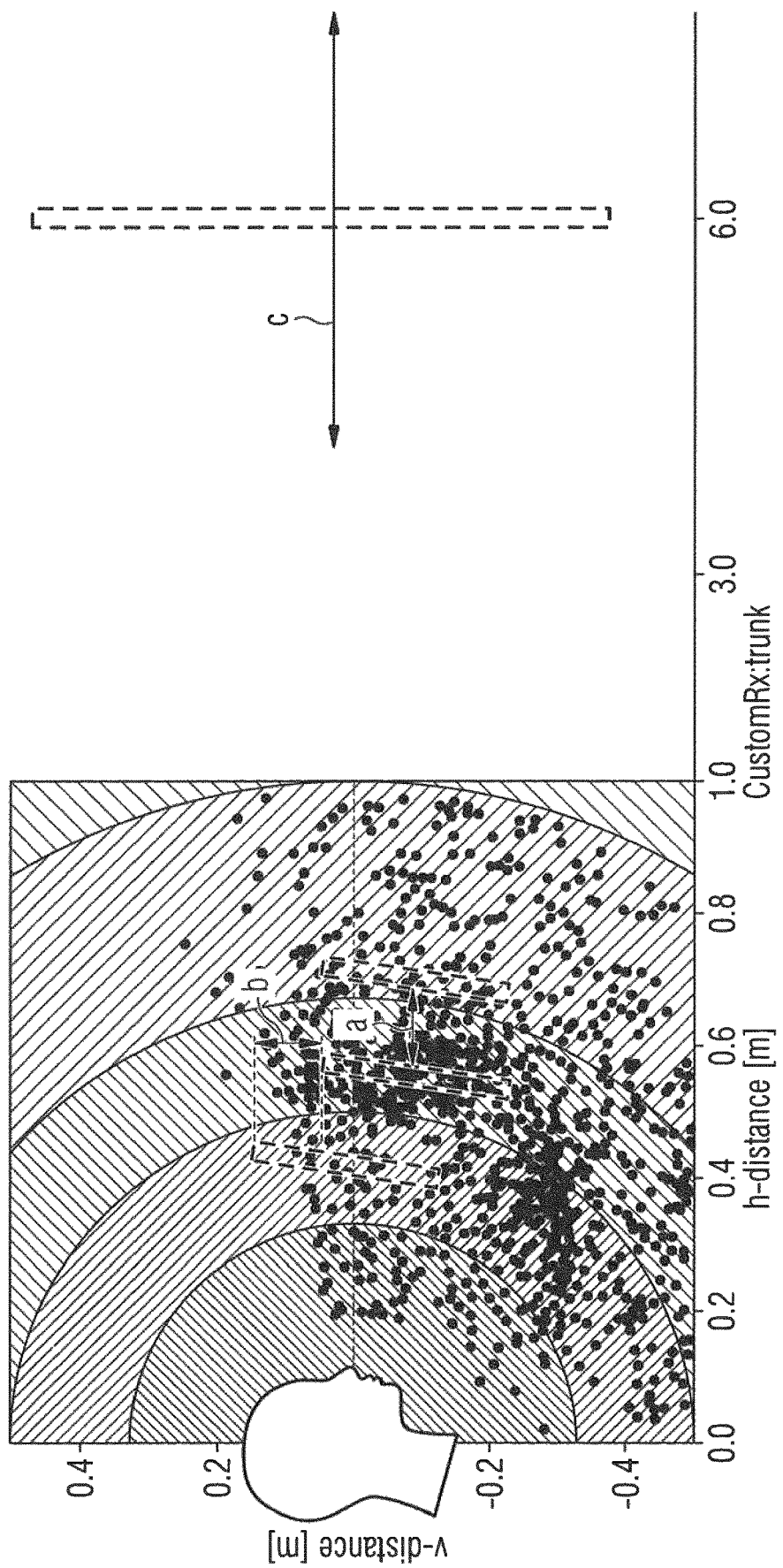
FIG. 16 illustrates examples of allowed offsets in 2-dimensional coordinates for reference data of example objects.

FIG. 16 illustrates examples of allowed offsets in 2-dimensional coordinates for reference data of example objects. Since characteristics of users and circumstances around the users may vary, it may be possible that the reference data cannot include sufficient data for all example objects depending on the varying characteristics and circumstances. Thus, when the measured data of the passive scanning device 100 are compared to the reference data, offsets between the measured data and the reference data may be allowed and the measured data in a range of the offsets may be determined to be matched to the reference data. As a result, lack of the reference data for certain varying characteristics and circumstances for an example object can be complemented.

For example, reference data for an object located between distances 0.4 m and 0.6 m may have allowed offsets 'a' in horizontal direction and 'b' in vertical direction. Allowed variations of object locations on the scene can be determined based on the statistics collected for the specific user as well as for multiple users. Variations for an example object usually located close to the user depending on the varying characteristics and circumstances may be comparatively small as compared to those of an example object located further away from the user. The allowed offset for the example object usually located at 6 m away from the user may be 'c' which may be greater than the value of 'a'. Vertical offsets for the example object located at 6 m away from the user may also be greater than the value of 'b'.

By way of the technique described herein, it is possible to scan objects of interest of a user without requiring complex devices and excessive computation in a processor. The disclosed device may be utilized to estimate the user's environment or activity in his/her daily life. Information on the user's environment or activity may be utilized to derive the user's vision needs for advising on refractive solutions.

It will be understood that the embodiments described above are merely exemplary and that the principles of the present disclosure may be practiced in other implementations.

It is believed that the advantages of the technique presented herein will be fully understood from the foregoing description, and it will be apparent that various changes may be made in the form, constructions and arrangement of the exemplary aspects thereof without departing from the scope of the disclosure or without sacrificing all of its advantageous effects. Because the technique presented herein can be varied in many ways, it will be recognized that the disclosure should be limited only by the scope of the claims that follow.

The invention claimed is:

1. An apparatus for passive scanning of at least one object, the apparatus comprising:
 a distance sensing unit adapted to measure distances to a plurality of points of the at least one object;
 an orientation sensing unit adapted to determine orientations of the distance sensing unit and/or a position sensing unit adapted to determine positions of the distance sensing unit; and
 a processor adapted to derive information about the at least one object based on the measured distances and the determined orientations and/or positions of the distance sensing unit;
 wherein the processor is adapted to:
 convert the measured distances and orientations and/or positions to a spatial model of the at least one object;
 compare the spatial model with stored reference spatial models; and
 classify the at least one object as one of example objects when a reference spatial model for the one example object has the largest matching score with the spatial model.

2. The apparatus of claim 1, wherein the information about the at least one object comprises or is at least one of a position, a shape, an inclination and a size of the object.

3. The apparatus of claim 1, wherein the distance sensing unit includes a plurality of distance sensors.

4. The apparatus of claim 1, wherein the apparatus is adapted to be equipped on a body part of the user.

5. The apparatus of claim 1, wherein the position sensing unit is adapted to measure at least one coordinate of the apparatus in space, wherein the position sensing unit includes at least one of a geolocation, an altimeter, an indoor positioning system and an hybrid positioning system.

6. The apparatus of claim 1, wherein the processor is adapted to:
 classify an activity of the user or an environment around the user from the derived information about the at least one object.

7. The apparatus of claim 1, further comprising:
 a motion sensor adapted to measure an amount of motion of the apparatus,
 wherein the processor is further adapted to discard distances and orientations and/or positions measured in a predetermined time period when the amount of motion measured by the motion sensor is higher than a threshold value.

8. The apparatus of claim 1, wherein the processor is adapted to classify the at least one object as one of the example objects when differences between the measured distances and orientations and/or positions and the stored reference distances and reference orientations and/or positions are smaller than predetermined amounts.

9. The apparatus of claim 8, further comprising:
 a memory unit adapted to store the reference spatial models.

10. A method for passive scanning of at least one object by a passive scanning device, the method comprising:
 measuring distances to a plurality of points of the at least one object;
 determining orientations and/or positions of the passive scanning device; and
 deriving information about the at least one object based on the measured distances and the determined orientations and/or positions;
 wherein the deriving information comprises:
 converting the measured distances and the determined orientations and/or positions to a spatial model of the at least one object;
 comparing the spatial model with stored reference spatial models; and
 classifying the at least one object as one of example objects when the reference spatial model for the one example object has the largest matching score with the spatial model.

11. The method of claim 10, wherein the orientations and/or positions are determined while the distances are measured.

12. The method of claim 10, wherein the information about the at least one object comprises or is at least one of a position, a shape, an inclination and a size of the at least on object.

13. The method of claim 10, further comprising:
 determining an activity of the user or an environment around the user from the derived information about the at least one object.

14. The method of claim 10, further comprising:
 estimating an activity-related viewing distance of the user by applying a statistical method to the derived information about the at least one object.

15. The method of claim 10, further comprising:
 identifying visual requirements of the user by applying a statistical method to the derived information about the at least one object.

16. The method of claim 15, wherein the identifying visual requirements comprises:
 identifying a user activity based on the derived information about the at least one object, and identifying the visual requirements based on the user activity; or
 identifying a user activity based on the derived information about the at least one object, identifying a viewing distance of a user based on the user activity, and identifying the visual requirements based on the viewing distance of the user.

17. The method of claim 10, further comprising:
 determining a refractive solution for the user based on the visual requirements,
 wherein the refractive solution is one of an ablation profile for refractive surgery, an ophthalmic implant and an ophthalmic lens,
 wherein the ophthalmic lens is one of an intraocular lens, a contact lens and a spectacles lens.

* * * * *